(12) United States Patent
Leyva

(10) Patent No.: US 10,264,913 B2
(45) Date of Patent: Apr. 23, 2019

(54) TECHNOLOGIES FOR SANITIZING BEVERAGE MAKERS

(71) Applicant: SoClean, Inc., Oxford, MA (US)

(72) Inventor: Timothy Leyva, Bellingham, MA (US)

(73) Assignee: SoClean, Inc., Peterborough, NH (US)

( * ) Notice: Subject to any disclaimer, the term of this patent is extended or adjusted under 35 U.S.C. 154(b) by 0 days.

(21) Appl. No.: 15/969,427

(22) Filed: May 2, 2018

(65) Prior Publication Data

US 2018/0310757 A1 Nov. 1, 2018

Related U.S. Application Data

(63) Continuation of application No. 15/498,884, filed on Apr. 27, 2017, now Pat. No. 9,986,871.

(51) Int. Cl.
| | | |
|---|---|---|
| *A61L 9/00* | (2006.01) | |
| *A47J 31/60* | (2006.01) | |
| *B08B 9/08* | (2006.01) | |
| *B08B 5/00* | (2006.01) | |

(Continued)

(52) U.S. Cl.
CPC ............. *A47J 31/60* (2013.01); *A61L 2/202* (2013.01); *A61L 2/26* (2013.01); *B08B 5/00* (2013.01); *B08B 9/08* (2013.01); *A61L 2202/11* (2013.01); *A61L 2202/123* (2013.01); *A61L 2202/13* (2013.01); *A61L 2202/14* (2013.01); *A61L 2202/15* (2013.01)

(58) Field of Classification Search
CPC .................................. A61L 2/00; A61L 2/202
USPC ........................................ 422/1, 28, 34, 305
See application file for complete search history.

(56) References Cited

U.S. PATENT DOCUMENTS

| | | | |
|---|---|---|---|
| 658,755 A | * | 10/1900 | Bowes, Jr. ............ F16L 37/252 |
| | | | 277/622 |
| 4,257,748 A | | 3/1981 | Ives et al. |
| 4,482,172 A | | 11/1984 | DeVera et al. |

(Continued)

FOREIGN PATENT DOCUMENTS

| | | |
|---|---|---|
| DE | 9104578.9 | 8/1992 |
| FR | 1529814 | 5/1968 |

(Continued)

OTHER PUBLICATIONS

Office Action dated Aug. 23, 2017, issued in U.S. Appl. No. 15/498,884, 8 pages.

(Continued)

*Primary Examiner* — Monzer R Chorbaji
(74) *Attorney, Agent, or Firm* — Grossman Tucker Perreault & Pfleger PLLC

(57) ABSTRACT

Technologies (e.g., devices, systems and methods) for sanitizing reservoirs are described. In some embodiments, the technologies include a sanitization gas system and a connector unit. The connector unit is configured to install into a portion (e.g., wall, bottom, top, or lid) of a reservoir, such as a reservoir of a hot beverage maker. The connector unit includes an inlet passageway for supplying sanitizing gas (e.g., ozone) into the reservoir, and an outlet passageway for removing sanitizing gas from the reservoir. In some embodiments at least a portion of the outlet passageway is disposed radially around the inlet passageway. The sanitization gas system may provide a sanitizing gas to the inlet passageway and receive the sanitizing gas from the outlet passageway.

28 Claims, 14 Drawing Sheets

(51) Int. Cl.
*A61L 2/20* (2006.01)
*A61L 2/26* (2006.01)

(56) References Cited

U.S. PATENT DOCUMENTS

| | | | |
|---|---|---|---|
| 4,762,343 | A | 8/1988 | Hirohata |
| 4,922,971 | A | 5/1990 | Grantham |
| 5,683,576 | A | 11/1997 | Olsen |
| 6,074,565 | A | 6/2000 | Buckner |
| 6,609,733 | B2 | 8/2003 | Gilmore |
| 7,240,700 | B2 | 7/2007 | Pangallo et al. |
| 7,472,929 | B2 | 1/2009 | Fattorusso et al. |
| 7,491,321 | B1 | 2/2009 | Maas et al. |
| 7,767,168 | B2 | 8/2010 | Namespetra et al. |
| 8,298,492 | B2 | 10/2012 | Shiotani et al. |
| 2003/0049164 | A1* | 3/2003 | Bon .................. A61L 2/183 422/28 |
| 2004/0051308 | A1 | 3/2004 | Coates |
| 2009/0039033 | A1 | 2/2009 | Kee et al. |
| 2010/0170857 | A1 | 7/2010 | Williams et al. |
| 2014/0154134 | A1 | 6/2014 | Leyva |
| 2015/0050194 | A1* | 2/2015 | Li ..................... A61L 2/202 422/186.12 |
| 2016/0102785 | A1 | 4/2016 | Bibbo et al. |
| 2016/0242596 | A1 | 8/2016 | Bennett |

FOREIGN PATENT DOCUMENTS

| | | |
|---|---|---|
| GB | 658755 | 10/1951 |
| WO | 2018200500 | 11/2018 |
| WO | 2018200504 | 11/2018 |
| WO | 2018200514 | 11/2018 |
| WO | 2018200519 | 11/2018 |

OTHER PUBLICATIONS

Office Action dated Aug. 23, 2017, issued in U.S. Appl. No. 15/499,070, 8 pages.
Office Action dated Aug. 30, 2017, issued in U.S. Appl. No. 15/498,954, 7 pages.
Notice of Allowance dated Dec. 14, 2017, issued in U.S. Appl. No. 15/499,070, 5 pages.
Notice of Allowance dated Dec. 18, 2017, issued in U.S. Appl. No. 15/498,954 5 pages.
Notice of Allowance dated Feb. 7, 2018, issued in U.S. Appl. No. 15/498,884, 5 pages.
Office Action dated May 7, 2018, issued in U.S. Appl. No. 15/928,287, 8 pages.
Office Action dated May 15, 2018, issued in U.S. Appl. No. 15/919,833, 8 pages.
International Search Report and Written Opinion dated May 21, 2018, issued in PCT Patent Application No. PCT/US2018/029127, 7 pages.
International Search Report and Written Opinion dated Jun. 4, 2018, issued in PCT Patent Application No. PCT/US2018/029133, 9 pages.
Office Action dated Oct. 29, 2018, issued in U.S. Appl. No. 15/499,167, 9 pages.
Office Action dated Oct. 29, 2018, issued in U.S. Appl. No. 15/919,833, 9 pages.
Office Action dated Dec. 4, 2018, issued in U.S. Appl. No. 15/928,287, 6 pages.

* cited by examiner

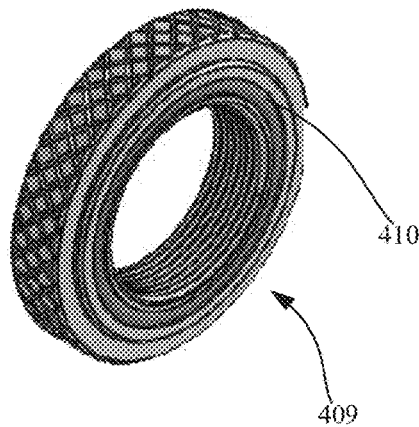 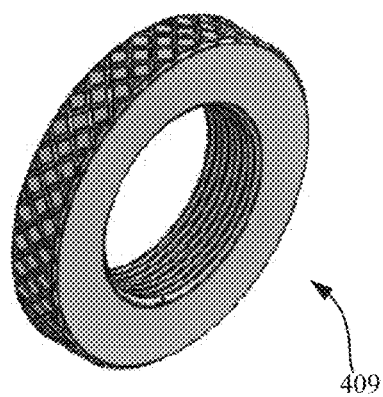
FIG. 4H                FIG. 4I
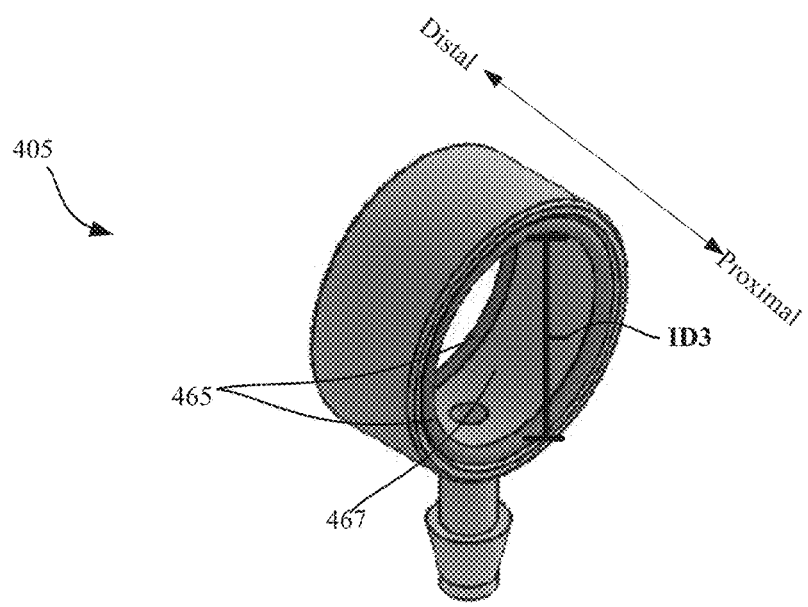
FIG. 4J

TECHNOLOGIES FOR SANITIZING BEVERAGE MAKERS

CROSS-REFERENCE TO RELATED APPLICATIONS

This application is a continuation of U.S. patent application Ser. No. 15/498,884, filed Apr. 27, 2017. The entire disclosure of which is incorporated herein by reference.

FIELD

The present disclosure generally relates to technologies for sanitizing beverage makers, including but not limited to hot beverage makers such as coffee and tea making machines. In particular, the present disclosure relates to devices and systems for sanitizing a water reservoir of a beverage maker (and optionally any water therein) with a sanitizing gas such as ozone. Methods of sanitizing a beverage maker are also disclosed.

BACKGROUND

Hot beverage makers (e.g., coffee and tea making machines such as the commonly used KEURIG® coffee maker) often have one or more reservoirs for holding water. In response to an input from a user, water in the reservoir may be drawn into a hot beverage maker and used to make a hot beverage of the user's choice.

Although many hot beverage makers are infrequently cleaned, users of such machines often assume that they are safe to drink from because the water they use is heated prior to being dispensed. This understanding may be incorrect, however, as many hot beverage makers do not heat water to a sufficiently high temperature (e.g. boiling) to adequately kill bacteria in the water prior to it being dispensed for consumption. Live bacteria and/or other contaminants may therefore remain in water that is dispensed by a hot beverage maker for consumption. Moreover, water in the reservoir of a hot beverage maker may also remain stagnant for long periods (e.g. days) before it is replaced or replenished with fresh water. This can provide an opportunity for mold and bacteria to build up on the walls and bottom of the reservoir, as well as in the water itself. Despite this risk, users of hot beverage makers often do not clean the reservoir or replenish the reservoir with fresh water when the water therein has been sitting for a long period of time.

The foregoing issues are compounded by the fact that many commonly recommended methods for cleaning hot beverage makers can be messy, time consuming, and inconvenient. For example, the user guide of some hot beverage makers may recommend cleaning the reservoir and/or other components of the machine using a cleaning solution that is a mixture of water and vinegar. Such methods can be inconvenient, as they often require the user to prepare the cleaning solution themselves. Moreover, such a cleaning solution may not effectively kill some types of water born mold and/or bacteria, and therefore may inadequately sanitize the reservoir of a hot beverage maker. Other commonly recommended methods of cleaning a hot beverage maker include manual washing, scrubbing, and drying of the reservoir, which are often time consuming and considered to be undesirable to consumers.

The inventors have, therefore, identified that there is a continued interest in the development of novel devices, systems, and methods for sanitizing all or a portion of a beverage maker, including but not limited to the water reservoir of a beverage maker and any water therein.

BRIEF DESCRIPTION OF THE DRAWINGS

Reference is now made to the following detailed description which should be read in conjunction with the following figures, wherein like numerals represent like parts:

FIGS. 4H and 4I are perspective views of the distal and proximal sides of an optional locking element consistent with the present disclosure.

FIG. 4J is a perspective view of a third connector portion consistent with the present disclosure

DETAILED DESCRIPTION

Figure 1:
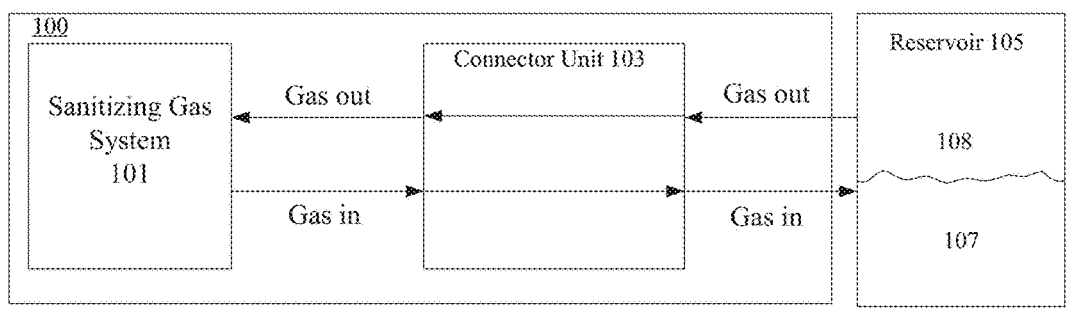
FIG. 1 is a block diagram illustrating sanitizing gas flow between a reservoir sanitization system and a reservoir, consistent with the present disclosure.

Consumers often believe that beverage makers (and in particular hot beverage makers) are safe to drink from, even though such machines may be rarely cleaned and may provide conditions that facilitate the growth of mold and/or bacteria. Although there are various known methods for cleaning beverage makers, such methods are often inconvenient, messy, time-consuming, etc., and therefore may be rarely performed by consumers. Such methods may also inadequately sanitize a beverage maker, and in particular the reservoir thereof and any water therein. The inventors have, therefore, identified that there is a need in the art for technologies (e.g., devices, systems and methods) that enable convenient, easy and effective sanitization of a beverage maker and, in particular, the reservoir of a beverage maker and any water therein.

With the foregoing in mind, aspects of the present disclosure relate to devices, systems and methods that utilize a sanitizing gas (e.g. ozone) to sanitize all or a portion of a beverage maker, such as but not limited to a reservoir thereof. For the sake of illustration the present disclosure focuses on embodiments in which the technologies described herein are employed to sanitize a water reservoir of a hot beverage maker. It should be understood that such examples are for the sake of illustration only, and that the technologies described herein may be used to sanitize a wide variety of reservoirs that may be used in applications other than a hot beverage machine. The technologies described herein are not limited to such applications, however, and can be utilized to sanitize any type of reservoir, such as those that may be used in soda fountains, animal watering machines, and the like.

Although the technologies described herein can be used with many sanitizing gases, the present disclosure focuses on the use of ozone as a sanitizing gas. This is because ozone ($O_3$) gas is an effective sanitizer, yet is relatively safe for consumer use. Indeed because of its strong oxidizing properties, ozone can effectively kill or otherwise remove a wide range of organic and inorganic contaminants such as yeasts, bacteria, molds, viruses, other pathogens, and/or pollutants with which it comes into contact, e.g., via oxidation. Yet naturally over time and/or as it oxidizes contaminants, ozone may be chemically reduced to oxygen ($O_2$), which is safe for human consumption and for release into the environment. Ozone is also relatively easy to generate on site (and thus does not require the use of a storage tank), and leaves little or no chemical residue. For those and other reasons, ozone has been identified as a safe and effective sanitizing gas for use in the present disclosure. It should be understood, however, that the technologies described herein are not limited to the use of ozone, and may be employed with a wide variety of sanitizing gases.

As used herein, the term "hot beverage maker" refers to any of a wide variety of machines that may be utilized to produce beverages for human or animal consumption, wherein the beverages are produced using water that is at a temperature that is greater than about 25 degrees Celsius, and which include a reservoir for holding water to be used by the machine. Non-limiting examples of hot-beverage makers include coffee making machines (e.g., the well-known KEURIG® coffee makers), espresso making machines, tea making machines, combinations thereof, and the like.

As used herein, the term "fluidly coupled" means that two or more components are connected to one another such that a gas may be conveyed between them. In contrast, the term "coupled" when used alone means that two or more components are connected to one another chemically (e.g., via an adhesive), mechanically (e.g., via fasteners, mechanical interference, etc.), or by other means.

One aspect of the present disclosure relates to systems for sanitizing a reservoir, such as but not limited to a reservoir of a beverage maker. As will be described further below, the systems described herein generally include a gas supply system, a connector unit, and an exhaust system.

The connector unit includes an inlet passageway and an outlet passageway, wherein the inlet passageway has a first proximal end and a first distal end, and the outlet passageway includes a second proximal end and a second distal end. The connector unit is configured to be installed within a portion of a reservoir, such as but not limited to a wall, cover, or bottom thereof. When so installed, the connector unit spans through a thickness of the portion of the reservoir such that the first and second distal ends are within an interior of the reservoir, and the first and second proximal ends are outside the reservoir. In embodiments, at least a portion of the outlet passageway is disposed radially around the inlet passageway. The gas supply system is configured to generate a sanitizing gas (e.g., ozone) and to fluidly couple to the first proximal end, such that sanitizing gas is conveyed through the inlet passageway into an interior of the reservoir. The exhaust system is configured to couple to the second proximal end, and to draw sanitizing gas (e.g. ozone) from the interior of the reservoir through the outlet passageway via the second distal end. In embodiments, the exhaust system includes a filter for converting or destroying the sanitizing gas that is removed from the interior of the reservoir.

FIG. 1 is a block diagram illustrating one example of the flow of sanitizing gas between a reservoir sanitization system consistent with the present disclosure and a reservoir. As shown, the reservoir sanitization system 100 includes a sanitizing gas system 101 and a connector unit 103. The sanitizing gas system 101 is fluidly coupled to the connector unit 103 such that it can provide a gas inflow (gas in) to the connector unit 103 and receive a gas outflow (gas out) from the connector unit 103. The connector unit 103 is fluidly coupled to a reservoir 105 including a liquid (e.g., water) 107. As shown, the sanitizing gas system 101 may supply an inflow of sanitizing gas (Gas in) such as ozone to the connector unit 103. The inflow of sanitizing gas passes through the connector unit 103 into the reservoir 105. More particularly, in embodiments the inflow of sanitizing gas is conveyed from the connector unit 103 to beneath a surface of the liquid 107 in the reservoir 107, as shown in FIG. 1.

At least a portion of the sanitizing gas supplied by the gas inflow may sanitize the liquid 107, as well as portions of the reservoir that are below the level of the liquid 107. In addition, at least a portion of the sanitizing gas supplied by the gas inflow may evolve from the liquid into the air 108 within the reservoir 105 and sanitize the portion of the reservoir 105 that is above the level of the liquid 107. Excess sanitizing gas within the reservoir 105 may be converted to another composition and/or be removed from the interior of the reservoir 105 via a gas outflow (gas out) through connector unit 103. More specifically, excess sanitizing gas may be conveyed via the gas outflow through the connector unit 103 and back to the sanitization gas system 101, as shown. In embodiments, the sanitizing gas system may be configured to remove the sanitizing gas and/or convert the excess sanitizing gas to another composition.

Figure 2:
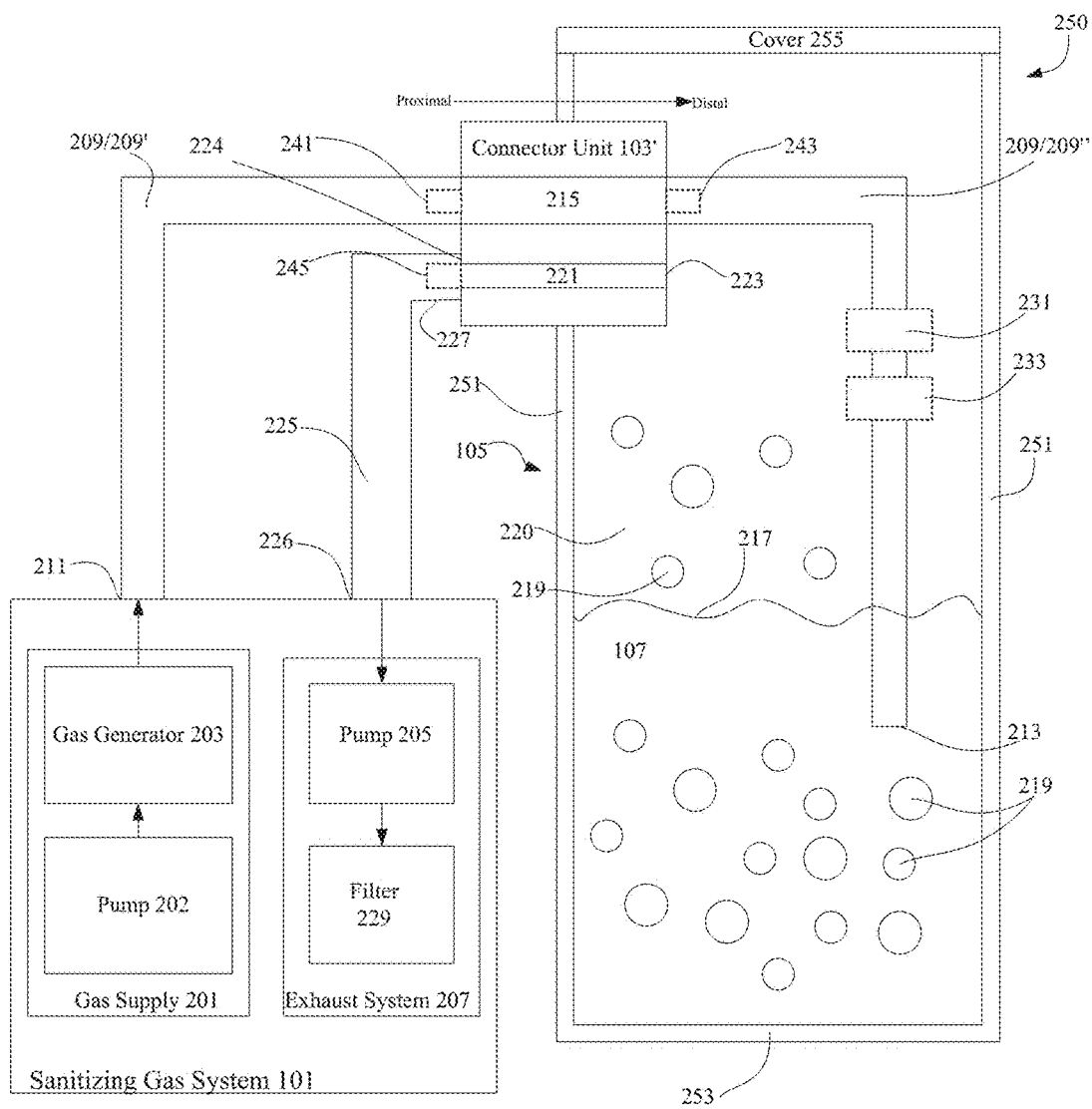
FIG. 2 is a block diagram of one example of a reservoir sanitization system consistent the present disclosure.

FIG. 2 is a block diagram of one example of a reservoir sanitization system 200 consistent with the present disclosure. As shown, the reservoir sanitization system includes a sanitizing gas system 101 that is fluidly coupled to a connector unit 103'. In this embodiment, the sanitizing gas system 101 includes a gas supply 201 including a pump 202 and a gas generator 203. The gas generator 203 is configured to generate a sanitizing gas, such as ozone or another sanitizing gas. The pump 202 (e.g., an air pump) is configured to generate a flow of air to convey the sanitizing gas to a proximal end 211 of supply line 209.

The connector unit 103' includes an inlet passageway 215 and an outlet passageway 221, wherein the inlet passageway includes first proximal and distal ends, and the outlet passageway 221 includes second proximal and distal ends. The connector unit 103' is generally configured to be installed within a portion of a reservoir, such as but not limited to a wall, bottom, top, or cover of a reservoir. When so installed, the connector unit 103' may span through a thickness of a portion of a reservoir, such that the first and second distal ends (of the inlet and outlet passageways 215, 221 respectively) are disposed within the interior of the reservoir, whereas the first and second proximal ends (of the inlet and outlet passageways) are disposed outside the reservoir.

That concept is shown in the embodiment of FIG. 2, which illustrates the connector unit 103' as being installed within a wall 251 of a reservoir 250 such that the distal ends (not labeled) of the inlet and outlet passageways 215, 221 are disposed within an interior of a reservoir 250, and the proximal ends (not labeled) of the inlet and outlet passageways (215, 221) are disposed outside the wall 251. As further shown, the reservoir may further include a bottom 253 and a cover 255, either of which may be acceptable locations for the installation of connector unit 103'. In embodiments, the cover 255 may not form a gas tight seal with the walls of the reservoir 250. In such embodiments the connector unit may be particularly configured for installation just below the cover 255 of reservoir 250, so as to enable the outlet channel 221 to remove sanitizing gas from the reservoir 250 prior to it can escape into the atmosphere through one or more openings/gaps in the connection/seal between the cover 255 and the walls of the reservoir 250.

As further shown in FIG. 2, the sanitizing gas system 101 (and, more particularly, the gas supply 201) is fluidly coupled to the connector unit 103' and/or the interior of the reservoir 250 via a supply line 209. In some embodiments the supply line 209 is configured to pass through the inlet passageway 215, such that a distal end 213 of the supply line is disposed within the interior of the reservoir 250. In some embodiments and as shown in FIG. 2, the distal end 213 may be located below a surface 217 of any liquid 107 that may be within the reservoir 250.

Alternatively in some embodiments first and second supply lines 209', 209" may be used instead of a single supply line 209. In such instances, the first supply line 209' may fluidly couple gas supply 201 with the first proximal end of the inlet passageway 215, and a proximal end of the second supply line 209" may be fluidly coupled to the first distal end of the inlet passageway 215. Coupling of the first and second supply lines 209', 209" to the inlet passageway 215 may be facilitated by optional first and second inlet connectors 241, 243, which are integral with or otherwise fluidly coupled to the first proximal and distal ends of the inlet passageway 215.

An optional check valve 231 may be provided on a distal portion of supply line 209 or on second supply line 209". When used, the optional check valve is generally configured to prevent a backflow of liquid 107 into the supply line 209 (or first and second supply lines 209', 209"). An optional sensor 233 may also be provided to sense a presence and/or concentration of sanitizing gas (e.g. ozone gas) within the interior of reservoir 250 and/or within connector unit 103'. In some embodiments the sensor 233 (when used) may be configure to provide a signal to a user interface, wherein the signal causes the user interface to indicate whether or not a safe level of the sanitizing gas is present in the reservoir 250, and/or to indicate when a beverage maker including the reservoir is safe to use.

The sanitizing gas system 101 further includes an exhaust system 207, which is fluidly coupled to a proximal end 224 of the outlet passageway 221 in the connector unit 103', in this case via a return line 225. The exhaust system includes a pump 205 and a filter 229. As shown, the return line 225 includes a proximal end 226 fluidly coupled to the exhaust system 207 (or, more particularly, to pump 205), and a distal end 227 coupled to the proximal end 224 of the outlet passageway 221. Coupling of the distal end 227 of the return line 225 to the proximal end of the outlet passageway 221 may be facilitated by an optional outlet connector 245 that is integral with or otherwise fluidly coupled to the proximal end of the outlet passageway 221.

In operation, gas generator 203 may generate a sanitizing gas 219 (e.g., ozone). Pump 202 (e.g., an air pump) may generate a flow of air to convey a sanitizing gas 219 into the supply line 209 (or first supply line 209', when used). In instances where a single supply line 209 is used, the sanitizing gas may 219 may flow through the supply line 209 such that it passes through the inlet passageway 215 and into the interior of the reservoir 250. Alternatively where first and second supply lines 209', 209" are used, the sanitizing gas 219 may flow through the first supply line 209', into the inlet passageway 215, and then into the second supply line 209". In either case, the sanitizing gas 219 may exit the distal end 213 of the supply line 209 (or second supply line 209").

When the distal end 213 is disposed beneath a surface 217 of a liquid 107 within the reservoir 250, the sanitizing gas 219 may be introduced into liquid 107. A portion of the sanitizing gas 219 may sanitize the liquid 107 and the parts of reservoir 250 that are below surface 217. At least a portion of the sanitizing gas 219 may also evolve from the liquid 107 into the air 220 within the reservoir 250, whereupon the sanitizing gas 219 may sanitize the air 220 and the interior surfaces of the walls 251 and cover 255. In instances where the distal end 213 is be disposed above surface 217, and/or no liquid 107 may be present within reservoir 250, the sanitizing gas 219 may sanitize the air and exposed surfaces of the walls 251, cover 255, and bottom 253.

During the sanitization of reservoir 250, all or a portion of the sanitizing gas 219 may be converted to another composition. For example in instances where the sanitizing gas is ozone, all or a portion of the ozone may be converted to oxygen during the sanitization of the reservoir 250. When excess sanitizing gas 219 is present within the air 220, it may need to be removed in order for the reservoir to be safely used. In that regard, pump 205 (e.g., a vacuum pump) may be configured to draw excess sanitizing gas 219 from the air 220 into the distal end 223, through the outlet passageway 221, and through the return line 114. The distal end 223 may be or include an opening that is fluidly coupled to (or configured to be fluidly coupled to) the interior of the reservoir 250. Sanitizing gas 219 removed from the interior of the reservoir 250 by the pump 205 may be conveyed to the filter 229.

The filter 229 may be configured to remove all or a portion of the sanitizing gas 219 conveyed thereto. For example, the filter 229 may be configured to absorb at least a portion of the sanitizing gas 219. Alternatively or additionally, the filter 229 may be configured to convert the sanitizing gas 219 to another composition, such as a composition that is safe for human inhalation and/or exhaust into the environment. In instances where the sanitizing gas 219 is ozone, for example, the filter 229 may be configured to convert all or a portion of the sanitizing gas to oxygen. Non-limiting examples of suitable filters that may be used as filter 229 include activated carbon filters, magnesium oxide filters, combinations thereof, and the like.

FIG. 2 depicts a reservoir 250 in combination with the reservoir sanitization system 200 for the sake of clarity and ease of understanding. It should be understood, however, that the reservoir sanitization systems described herein need not include the reservoir. The systems described herein may also be used with any suitable reservoir, and are not limited to use with reservoirs consistent with those illustrated in the figures.

FIG. 2 also depicts one example embodiment of a system utilizing a connector unit 103' that includes inlet and outlet passageways 215/2211 that are laterally offset from one another. It should be understood that such illustration is for the sake of example only, and that other connector units may be used in the technologies of the present disclosure. Indeed as will be described later in connection with FIGS. 3-6B, the technologies described herein may include and/or utilize a connector unit that includes an inlet passageway and an outlet passageway, wherein at least a portion of the outlet passageway is disposed radially around the inlet passageway. For ease of reference, such connector units are referred to herein as a "double wall connector unit."

Figure 3:
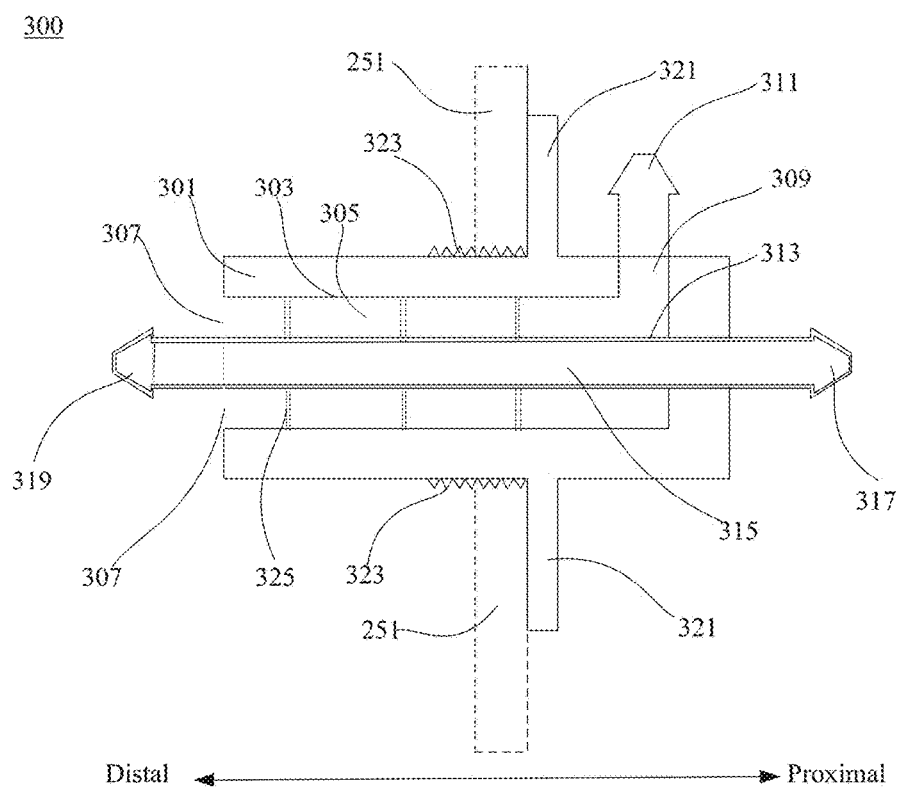
FIG. 3 is a cross sectional view of one example of a double wall connector unit consistent with the present disclosure.

FIG. 3 is a cross sectional diagram of one example of a double wall connector unit consistent with the present disclosure. As shown, double wall connector unit 300 includes an outer wall 301 and an inner wall 313, both of which are tubular or cylindrical in shape. An inlet passageway 315 is defined in the inner wall 313 and extends from a first inlet connector 317 to a second inlet connector 319. The outer wall 301 includes an inner surface 303 and the inner wall 313 has an outer surface 314. An outlet passageway 305 is defined between the inner surface 303 and the outer surface 314. Thus, at least a portion of the outlet passageway 305 is disposed radially around the inlet passageway 315.

The outlet passageway 305 extends from an opening 307 at a distal end thereof to an outlet connector 311, which is disposed near a proximal end of the connector unit 300. In some embodiments, optional spacer elements 325 may be disposed between the inner wall 313 and the outer wall 301. When used, the optional spacer elements 325 may be configured to maintain a gap forming a portion of the outlet passageway between the inner wall 313 and the outer 301.

The double wall connector unit 300 further includes a flange 321 and coupling elements 323. The coupling elements 323 are generally configured to facilitate the installation of the double wall connector unit 300 into a portion of a reservoir. To illustrate that concept, FIG. 3 depicts double wall connector unit 300 as installed into a wall 251 of a reservoir. In the illustrated embodiment, coupling elements 323 are configured as teeth, threads, or other mechanical coupling elements that engage with an inward facing surface of an opening (not shown separately) in the wall 251.

In some embodiments the coupling elements 323 are self-tapping threads that are configured to form and threadably engage with threads in an inward facing surface of the wall 251 or another portion of a reservoir. For example, following the provision of an unthreaded pilot hole in wall 251, distal end of the double wall connector unit 300 may be inserted into the pilot hole. During such insertion the double wall connector unit 300 may be rotated about an axis extending through and parallel with the inlet passageway 317. While the double wall connector unit 300 is rotated the coupling elements 323 (e.g., self-tapping threads) may engage the inward facing surface of the pilot hole and form corresponding threads therein as the double wall connector unit 300 is advanced therein. Advancement of the double wall connector unit 300 may continue until a distal surface of the flange 321 contacts a portion of the wall 251 about the hole, at which time the double wall connector unit 300 may be considered to be in an installed position.

Of course, use of self-tapping threads and an unthreaded pilot hole is not required. For example, in some embodiments a pre-threaded pilot hole may be provisioned in wall 251. In such instances the distal end of the double wall connector unit 300 may be inserted in the pre-threaded hole. The double wall connector unit 300 may then be rotated to threadably engage the coupling elements 323 with the threads of the pre-threaded hole, so as to advance the distal end of the double wall connector unit 300 until the distal surface of the flange 321 contacts a portion of the wall 251 about the pre-threaded hole.

While the embodiment of FIG. 3 is useful (particularly in instances where a double wall connector unit is to be installed by a manufacturer of a reservoir), consumers may be unable to provide a pilot hole in a reservoir or may find it inconvenient to do so. Connector units that are capable of forming their own hole in a portion of a reservoir own may therefore be desired. Such connector units are referred to herein as a "self-drilling" connector unit. It is noted that the term "self-drilling" is used herein to refer to the general capability of a connector unit to form a hole in a portion (e.g., wall, bottom, top, or lid) of a reservoir, but is not used to limit the manner in which that hole is formed. Thus while in some embodiments the self-drilling connector units described herein may be configured to form a hole in a reservoir by "drilling," they are not limited to such modalities. For example, the self-drilling connector units may be configured to form a hole in a reservoir by cutting, drilling, punching, coring, combinations thereof, and the like.

Figure 4A:
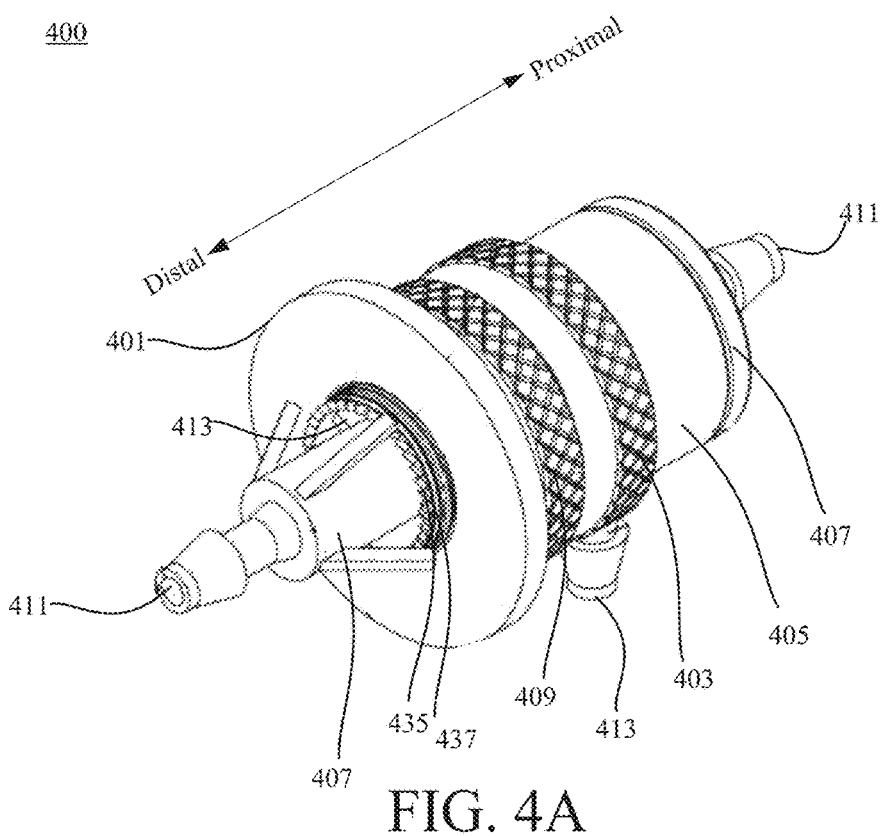
FIG. 4A is a perspective view of another example of a double wall connector unit consistent with the present disclosure.
Figure 4B:
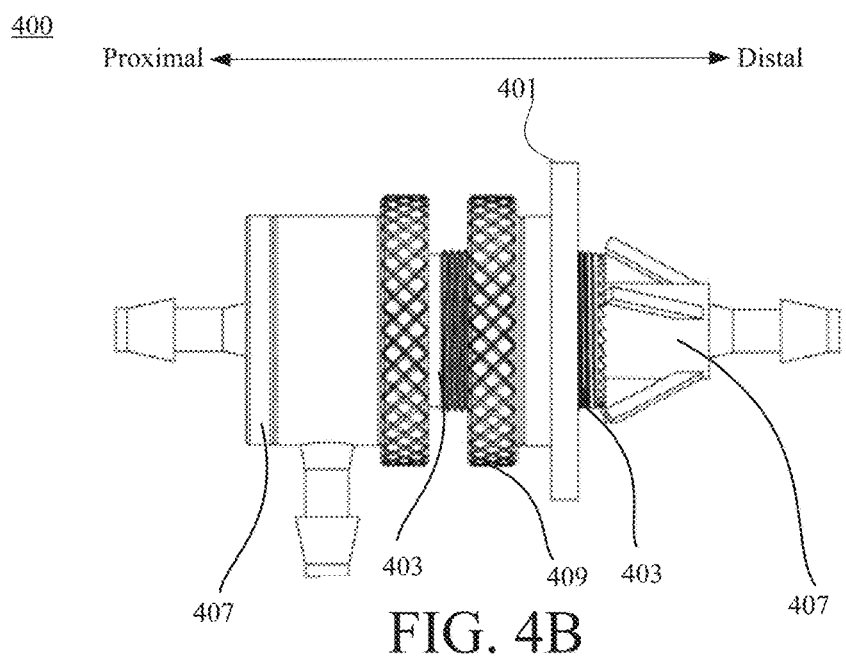
FIG. 4B is a front view of the double wall connector unit of FIG. 4A.
Figure 4C:
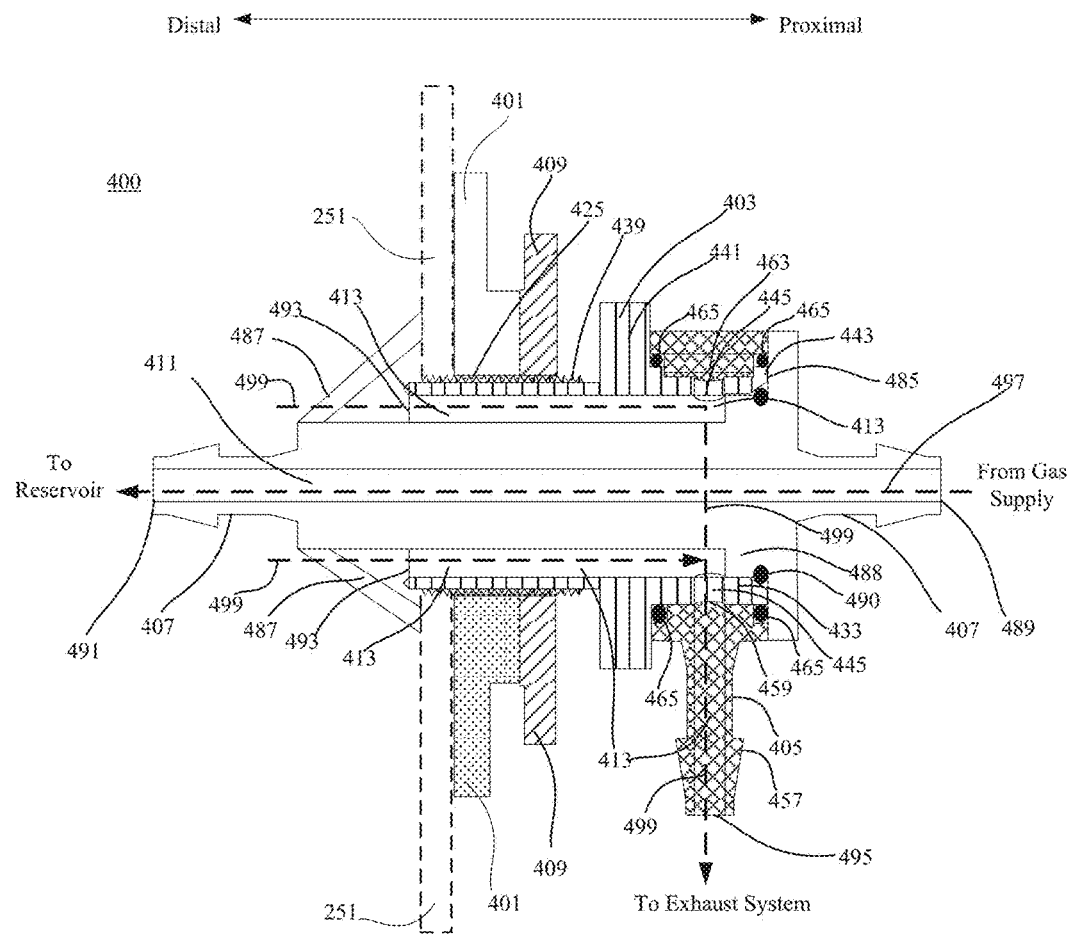
FIG. 4C is a cross-sectional view of the double wall connector unit of FIG. 4A.
Figure 4D:
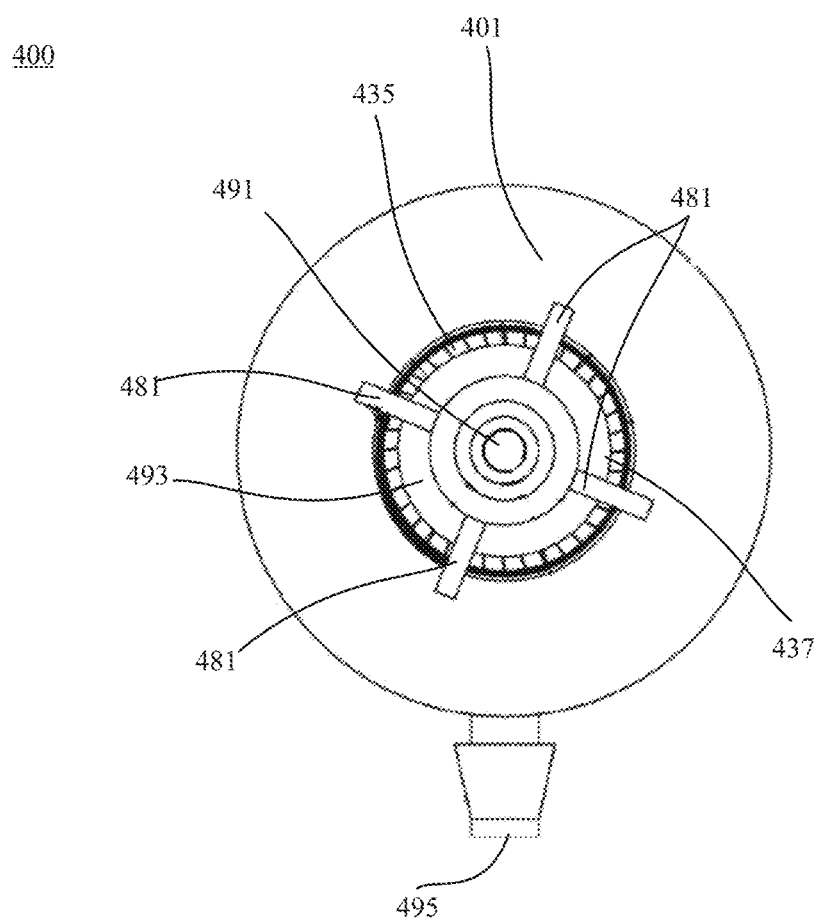
FIG. 4D is a front view of the double wall connector unit of FIG. 4A.
Figure 4E:
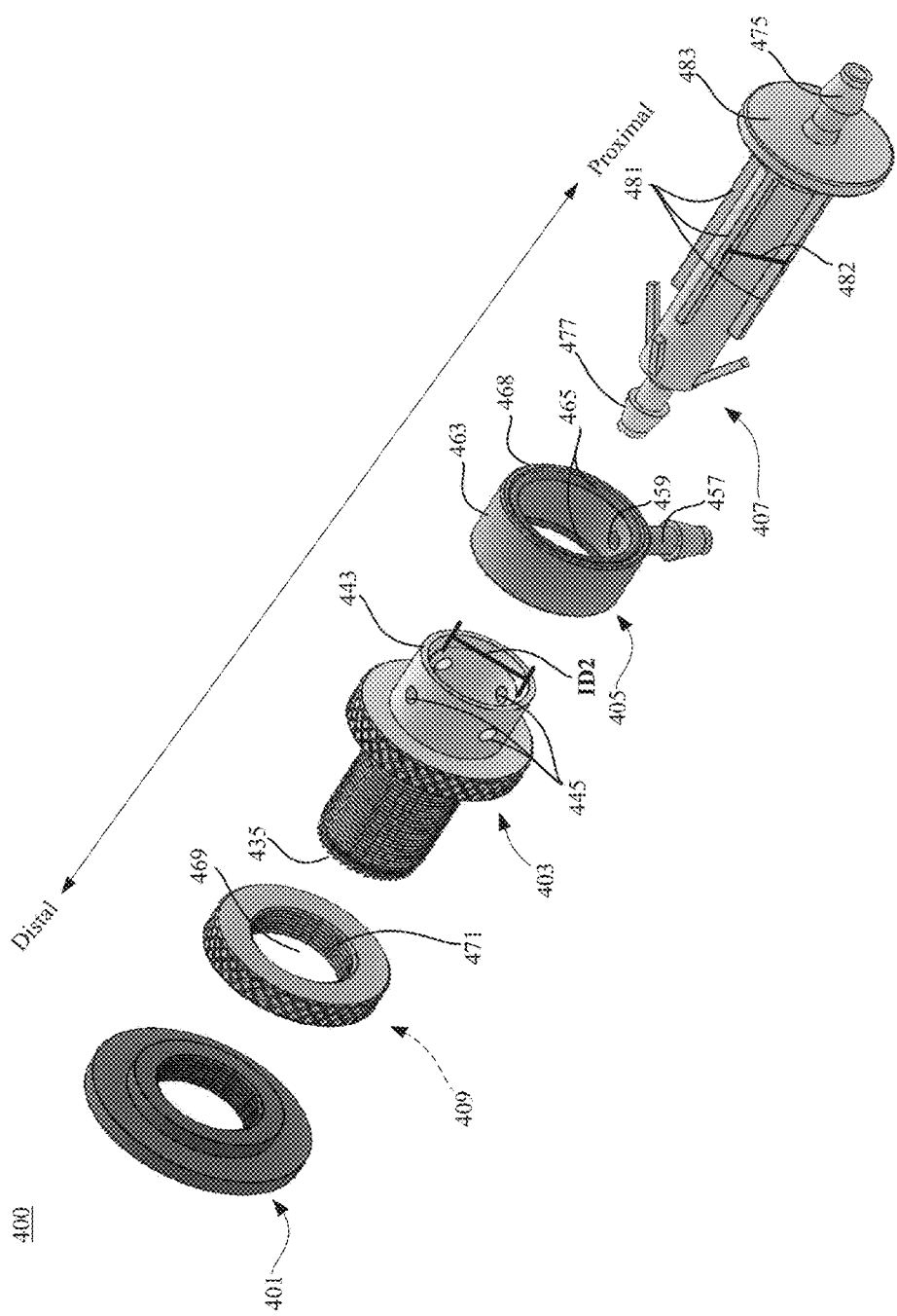
FIG. 4E is an exploded perspective view of the double wall connector unit of FIG. 4A.

FIGS. 4A-4K depict various views of one example of a self-drilling double wall connector unit 400 (hereinafter, connector unit 400) consistent with the present disclosure, as well as components thereof. As best shown in FIG. 4E, connector unit 400 includes a first connector portion 401, a second connector portion 403, a third connector portion 405, a fourth connector portion 407, and an optional locking element 409. Such components are generally configured to provide an inlet passageway for the provision of a sanitizing gas into a reservoir, and an outlet passageway for the removal of the sanitizing gas from the reservoir. In addition, the connector unit 400 is configured such that it forms a hole in a portion of a reservoir as it is installed therein.

Figure 4F:
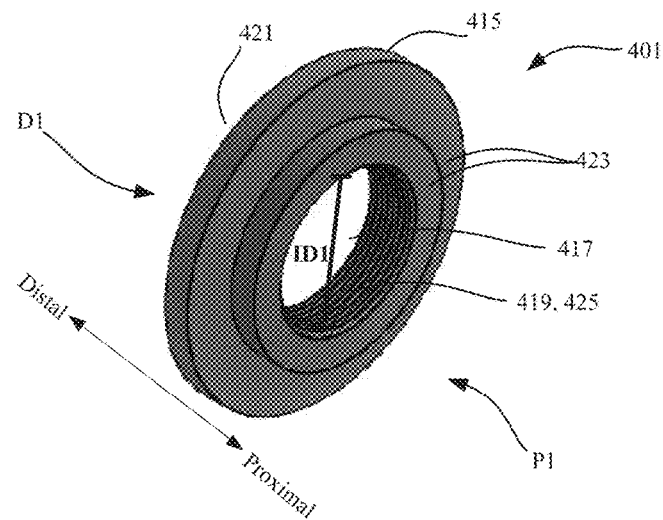
FIG. 4F is a perspective view of a first connector portion consistent with the present disclosure.

As best shown in FIG. 4F, the first connector portion 401 includes a first (e.g., tubular, circular or cylindrical) body 415 having a proximal end P1 and a distal end D1. An opening 417 is defined at least in part by an inner surface 419 of a wall of the first body 415 and extends from the proximal end P1 to the distal end D1. In general, the first connector portion 401 is configured to couple or be coupled to a wall (e.g., wall 251) or another portion of a reservoir, e.g., via an adhesive, tape, mechanical fasteners, or some other means (not shown).

In some embodiments the first connector portion 401 includes an inward facing surface 421 and an outward facing surface 423. The inward facing surface 421 is configured to face toward a portion of a reservoir, such as but not limited to wall 251 when the first connector portion 401 is coupled thereto. In contrast, the outward facing surface 423 is configured to face away from the (e.g., wall of) reservoir. Although not shown, the first connector portion 401 may also include a first sealing element that is configured to be disposed between the inward facing surface 421 and a wall of a reservoir. When used, the first sealing element may be configured to form a liquid and/or gas tight seal between the first connector portion 401 and a wall of the reservoir when the first connector portion 421 is urged against that wall. One example of a suitable first sealing element is an O-ring seal, which may be at least partially disposed within a groove (not shown) in the inward facing surface 421 of the first connector portion that is formed around the opening 417. Of course, other types of sealing elements may also be used.

The opening 417 may include first guide elements 425 therein. The first guide elements 425 are generally configured to guide at least a portion of the second connector portion 403 when it is inserted into the opening 417. For example and as shown in FIG. 4F, the first guide elements 425 may be internal female threads formed in at least a portion of the inner surface 419. In such instances the first guide elements 425 may be configured to threadably couple with corresponding second guide elements 439 (e.g., outer male threads) on the second connector portion 403, as best shown in FIG. 4C. More specifically, the first guide elements 425 may be configured to threadably engage second guide elements 439 of the second connector portion 403, thereby coupling the first connector portion 401 to the second connector portion 403 and drawing the second connector portion 403 into the opening 417.

Figure 4G:
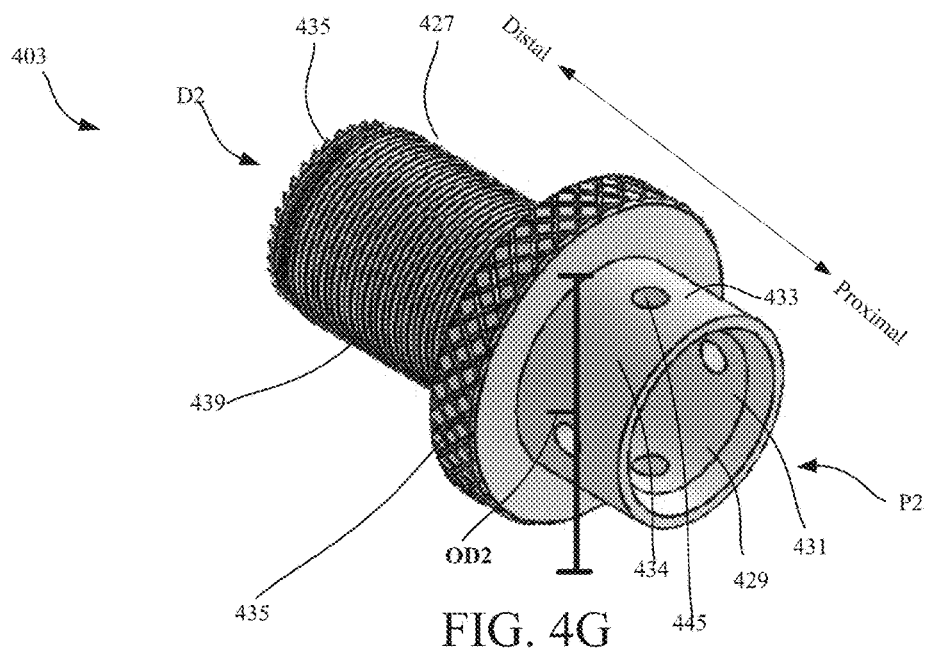
FIG. 4G is a perspective view of a second connector portion consistent with the present disclosure.

As best shown in FIGS. 4A, 4E, and 4G, the second connector portion 403 includes a second (e.g., tubular, circular or cylindrical) body 427 that has a proximal end P2 and a distal end D2. A first passageway 429 is defined at least in part by an inner surface 429 of a wall 433 of the second body 427, and extends from the proximal end P2 to the distal end D2 of the second body 427. Self-drilling elements 435 may be coupled to or integral with at least a portion of the distal end D2/edge of the second body 427, as best shown in FIGS. 4A, 4D, 4E, and 4F. For example and as best shown in FIG. 4A, the distal end D2 of the second body 427 may include a circumferential edge 437 that extends around the distal end D2 of the first passageway 429 (and, hence, outlet passageway 413), wherein self-drilling elements 435 (e.g., cutting/drilling/abrading teeth, blades, surfaces, etc.) may be disposed on or integral with a facing surface of the circumferential edge 437.

At least a portion of the second body 427 is configured to be disposed within the opening 417 of the first connector portion 401. In that regard at least a portion of the opening 417 of the first connector portion 401 may have an inside diameter ID1 that is larger than an outside diameter OD2 of at least a portion of the second body 427. As a result, at least a portion of the second body 427 may be inserted into the opening 417 of the of the first connector portion 401.

Second guide elements 439 (e.g., male or female threads) may be disposed on or integral with a portion of an outer surface of the second body 427. The second guide elements 439 are generally configured to interact with the first guide elements 425 of the first connector portion 401, as best shown in FIG. 4C. In that manner, the first and second guide elements 425, 439 may guide and urge the self-drilling elements 435 into contact with a wall (e.g., wall 251) or another portion of a reservoir.

For example when the first and second guide elements 425, 439 are female and male threads, respectively, the second connector portion 403 may be configured such that when the distal end D2 is inserted into the opening 417 and the second connector portion 403 is rotated, the second guide elements 439 threadably engage with the first guide elements 425 so as to draw the distal end D2 into the opening 417 and ultimately into contact with a portion (e.g., wall 251) of a reservoir. Further rotation of the second connector portion 403 may cause the self-drilling elements 435 to form a hole in a portion (e.g., wall 251) of the reservoir, wherein the hole has an inward facing surface.

Rotation of the second connector portion 403 may also cause the second guide elements 439 to engage and/or contact at least a portion of the inward facing surface of the hole formed in the reservoir by the self-drilling elements 435. For example, in instances where the second guide elements 439 are male threads (e.g., self-tapping threads), such threads may create and engage with corresponding female threads in the inward facing surface of the hole, e.g., during or after formation of the hole by the self-drilling elements 435.

The second connector portion (and, more particularly, the second guide elements 439) may thus be configured to form and engage with corresponding threads on the inward facing surface of a hole through a wall, bottom, or lid of a reservoir, thereby coupling the second connector portion 403 to the reservoir. The second connector portion (and, in particular, the second guide elements 439) may also be configured to urge the first connector portion 401 against an outer surface of the reservoir (e.g., an outer surface of wall 251) that is around the hole.

The second connector portion 403 may also include a handle. The handle may be configured to help a user to grip and rotate the second connector portion 403 during its installation into a reservoir. The type and nature of the handle is not limited, provided it can facilitate the rotation of the second connector portion 403 about an axis extending through and parallel to the first passageway 429. With that in mind, the embodiment of FIGS. 4A-4K depict one example of a connector unit that includes a knurled handle 441 that is integral with or coupled to an intermediate portion of the second body 427, extends around the circumference of the second body 427, and is located proximal to the second guide elements 439.

The use of knurled handle 441 is of course for the sake of example only, and it should be understood that any suitable handle may be used, and that handle 441 (or another handle) may be positioned at any suitable location. Without limitation, in some embodiments the second connector portion 403 includes a handle that is coupled with or integral to an intermediate portion of second body 427, such that the handle is disposed outside a reservoir when the second connector portion 403 is in an installed position.

The second connector portion 403 further includes one or more abutment surfaces 443. The abutment surface 443 is generally configured to abut against a corresponding engagement surface 485 of the fourth connector element 407 when the fourth connector element is in an installed position, as will be further described below. That concept is best shown in FIG. 4C, which depicts abutment surface 443 abutting (e.g. contacting) engagement surface 485 of the fourth connector portion 407 when the fourth connector portion is in an installed position.

The second connector portion 403 further includes at least one proximal opening formed in a wall 433 of the second body 427. In general, the proximal opening is configured to fluidly couple to an outlet port, so as to provide at least a portion of the outlet passageway 413 for the removal of gas (e.g., ozone) from a reservoir. That concept is shown in FIGS. 4C and 4E, which illustrate an embodiment in which a plurality of proximal openings 445 are formed through the wall 433, wherein at least one of the proximal openings is in fluid communication with an outlet port 457 on the third connector portion 405.

The connector units described herein may of course include greater or fewer proximal holes. When more than one proximal hole is used, all or less than all of such proximal holes may be in fluid communication with an outlet port. That concept is shown in FIG. 4G, which depicts four proximal openings 445 in the second body 427. As shown in FIG. 4C, some the proximal opening(s) 445 are fluidly coupled to outlet port 457, e.g., via a circumferential gap between an inner surface of the second body portion 403 and an outer surface of the third body portion 405.

The location and configuration of the proximal opening(s) formed in the second body 427 is not particularly limited, provided that it is (or they are) positioned such that it remains (or they remain) on the outside of a reservoir when all elements of the connector unit 400 are in an installed position, and provided that one or more than one proximal opening is in fluid communication with an outlet port and at least a portion of an outlet passageway that is present between the second connector portion 403 and the fourth connector portion 409. Put in other terms, the second connector portion 403 may include at least one proximal opening 445 that fluidly couples at least a portion of an outlet passageway 413 that is present between the second connector portion and the fourth connector portion to one or more outlet ports.

It is noted that in the embodiment of FIGS. 4A-4K, outlet port 457 and the third body 463 are depicted as components that are separate from the second connector portion 403. In such instances it should be understood that the outlet port 457 and third body 463 may be integral with or coupled to the third connector portion 405. As shown in FIGS. 4C and 4E for example, the third connector portion 405 may comprise the third body 463 and the outlet port 457. In the illustrated embodiment, the third body 463 has a hollow tubular shape with an inside diameter ID3 that is larger than the outside diameter OD2 of a proximal portion of the second connector portion 403.

At least a portion of the third body 463 may thus be configured such that it may slide over a proximal portion of the second connector portion 403, e.g., until a distal facing surface (not labeled) thereof abuts a proximal facing surface of a portion of the second connector portion, e.g., a proximal facing surface (not labeled) of handle 441. Put in other terms, the third body 463 may include or be in the form of a collar having an outer wall and an opening, wherein the collar is configured to be disposed around a proximal end P2 of the second connector portion 403.

The third body 463 may also include an outlet opening 459 that is fluidly coupled to outlet port 457, which is integral with or coupled to third body 463 in any suitable manner. As best shown in FIG. 4C, when the third connector portion 405 is in an installed position (e.g., after third body 463 is slid over a proximal portion of the second connector portion 403 such that a distal face of the third body 463 abuts a proximal face of the handle 435 of the second connector portion 403), the outlet opening 459 may be aligned with one or more of the proximal openings 445 in the second body 427.

Alternatively or additionally, one, more than one, or all of the proximal openings 445 may be in fluid communication with the outlet port opening 459, regardless of whether they are aligned with the outlet port opening or not. In that regard, one or more spacer elements 465 may be disposed within the opening in the third body 463, e.g., as shown in FIGS. 4E and 4J. The spacer elements 465 may be laterally spaced from one another, and may be generally configured to abut with a portion of an outer surface of the second body 427. In addition, the spacer elements 465 may be configured such that a gap is maintained between them, and also between an inward facing surface 467 of the third body 463 and an outward facing surface 434 of a proximal portion of the wall 33 of the second connector portion 403. Put in other terms, the spacer elements 465 may facilitate the maintenance of a circumferential gap between the inward facing surface 467 the outward facing surface 434, wherein the circumferential gap may form part of the outlet passageway 413 for the removal of gas (e.g., ozone) from a reservoir.

Although not shown in the figures, in some embodiments the third connector portion 405 may be omitted. In such embodiments the third body 463 and outlet port may be integral with or otherwise coupled to second connector portion 403 in any suitable manner. For example, the outlet port 457 and third body 463 may be mechanically coupled to the second connector portion 403, e.g., with one or more adhesives, mechanical fasteners, welds, interference fittings press fittings, combinations thereof, and the like. In such instances, one or more spacer elements may be disposed between the inward facing surface of the third body 463 and the outward facing surface 434 so as to maintain a circumferential gap between such elements, as previously described. Alternatively or additionally, the outlet port 457 and third body may be integral with the second connector portion 403, in which case they may be configured to maintain the circumferential gap in any suitable manner.

In some embodiments the connector unit 400 may include an optional first locking portion 409. When used, the first locking portion 409 is configured to fix (i.e., lock) the position of the first connector portion 401 relative to the second connector portion 403, e.g., once the second connector portion 403 is in an installed position. In addition, in some embodiments the first locking portion 409 may also serve to further urge and/or secure the first connector portion 401 against and/or to an outside surface of the reservoir, such as the outside of a wall 251 of a reservoir as shown in FIG. 4C.

FIG. 4E illustrates one example of a connector unit 400 that includes an optional first locking element 409. In the illustrated embodiment the first locking element 409 is in the form of a threaded nut that is includes an opening 469 and threads 471 on an inward facing surface thereof. The threads 471 are configured to engage with the second guide elements 439 (e.g., threads) on an outer surface of the second body 427. That is, threads 471 may threadably coupled to second guide elements 439. Prior to insertion of the second connector portion 403 into the opening 417, first locking element may be positioned relatively close to the proximal end P2 of the second body. This may be accomplished, for example, by rotating the first locking element 409 relative to the second connector portion 403 while the threads 471 are engaged with the second guide elements 439.

Following insertion of the second connector portion 403 into the opening 417, the second connector portion 403 may be rotated to form a hole in a portion of a reservoir (e.g., wall 251). Subsequently (e.g., when the second connector portion is in an installed position), the first locking element 409 may be rotated about an axis extending through and parallel to the second body 427, so as to draw the first locking element 409 towards the distal end D2 of the second connector portion 403 until a surface of the first locking element 409 is adjacent to and/or in contact with a portion of the outward facing surface 423 of the first connector portion 401. Once the first locking element 409 is so positioned, movement of the first connector portion 401 relative to the second connector portion 403 may be hindered and/or prevented. In that way, first locking element 409 may "lock" the position of the first connector portion 401 relative to the second connector portion 403.

FIGS. 4H and 4I show the distal and proximal ends, respectively, of one example of a first locking element 409 consistent with the present disclosure. As shown, the first locking element 409 may further include a sealing element 410 disposed on or in proximity to the radial edge of the distal end of the locking element 409. In general, the sealing member (e.g., an O-ring) may be configured to facilitate sealing of the distal end of the locking element 409 against a proximal surface of the first connector portion 401, e.g., to form a gas tight seal.

In some embodiments the connector units described herein may include multiple locking elements. As one example of that concept reference is made to FIGS. 6A and 6B. Such FIGS. depict a connector unit 400' that is substantially similar to connector unit 400, except that it includes both a first locking element 409 and a second locking element 409'.

Similar to connector unit 400, installation of the connector unit 400' may begin by coupling first connector portion 401 to a portion (e.g., wall 251) of a reservoir. First locking element 409 may be moved (or may have been previously moved) to a proximal position along the outside surface of the distal portion of the second connector portion 403, as previously described. The distal end D2 of the second connector portion 403 may be inserted into an opening in the first connector portion 401, and the second connector portion 403 may be rotated to cause self-drilling elements 435 to form a hole in the (e.g., wall 251) of the reservoir.

Figure 6A:
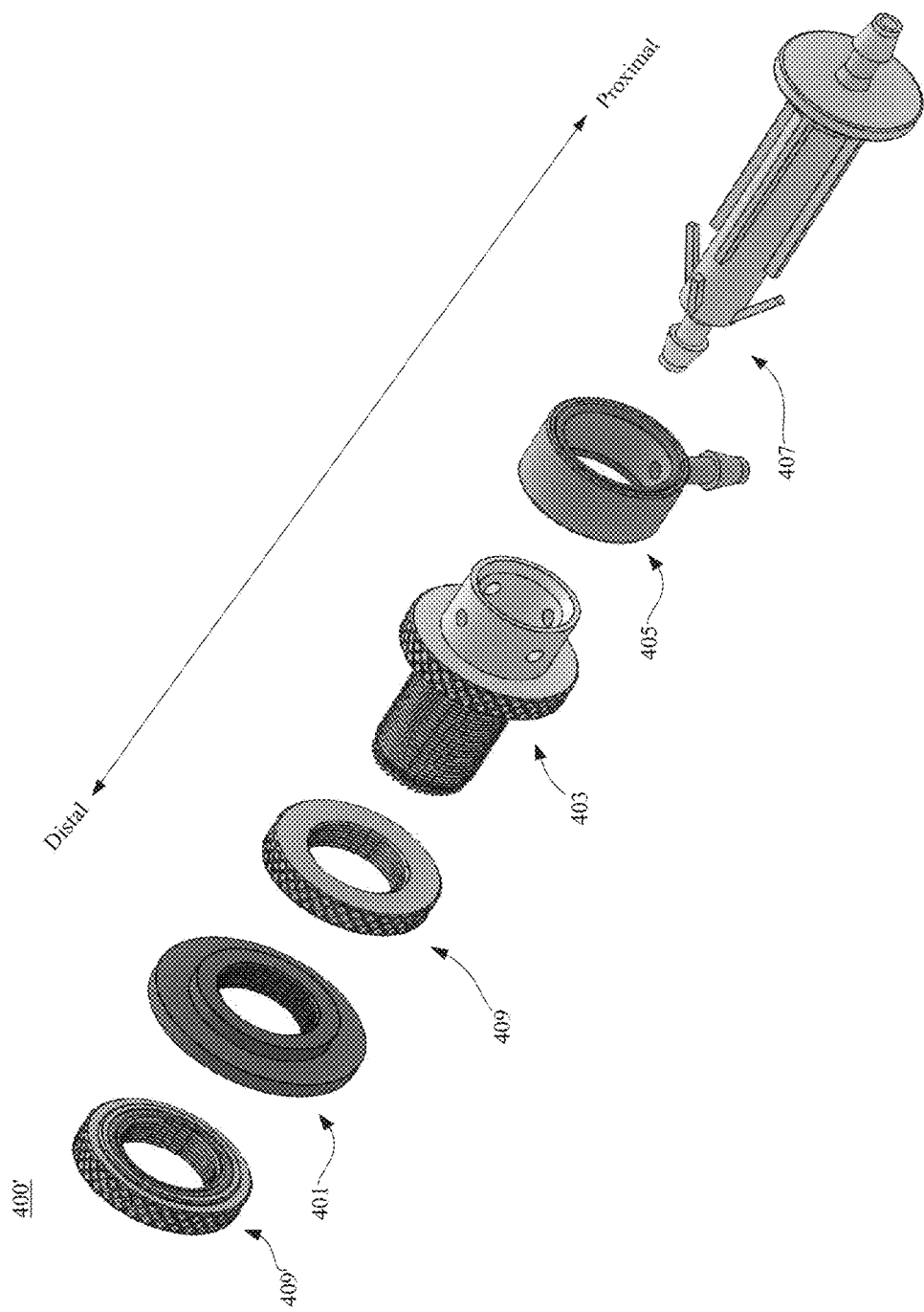
FIG. 6A is a perspective exploded view of another double wall connector unit consistent with the present disclosure.
Figure 6B:
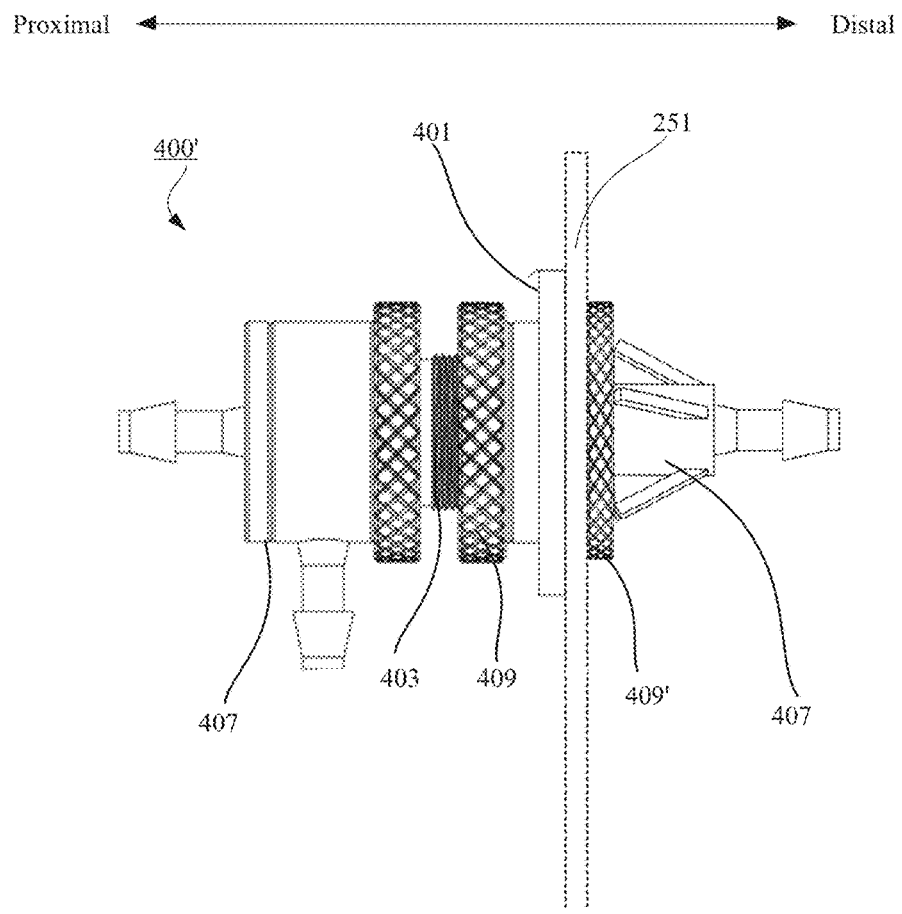
FIG. 6B is a side view of the double wall connector unit of FIG. 6A.

In the embodiment of FIGS. 6A and 6B the second connector portion 403 may be configured such that rotation of the second connector portion 403 eventually causes the distal end D2 thereof to protrude into the reservoir. To accomplish this, the length of the distal end D2 of the second connector portion may be configured such that it is greater than a thickness of the wall, bottom, or lid of a reservoir. That concept is shown in FIG. 6B, which depicts connector unit 400' as installed through a wall 251 of a reservoir.

In the embodiment of FIGS. 6A and 6B the second locking element 409' is configured in substantially the same manner as the first locking element 409. As a result, the second locking element 409' may include an opening having an inward facing surface with threads or other guide elements that are configured to engage second guide elements 439.

In instances where the second guide elements (on an outward facing surface of a wall of the second connector portion 403) are threads, the second locking element 409' may (like the first locking element 409) include corresponding threads. In such instances, the threads of the second locking element 409' may engage with the second guide elements 439, such that rotation of the second locking element 409' draws it along the outside of second body 427, e.g., until the second locking element 409' abuts and/or is in contact with an inward facing surface of the reservoir (e.g., and inward facing surface of wall 251. That concept is shown in FIG. 6B, which shows connector unit 400' installed in a wall 251 of a reservoir, with first and second locking elements 409, 409' disposed on outer and inward facing sides of the wall 251. An optional sealing element 410 may also be disposed on one side of the second locking element 409' to facilitate the formation of a seal with an inward facing surface of the reservoir, e.g., in the same manner shown in FIG. 4H.

Returning to FIGS. 4A-4K, the connector unit 400 further includes a fourth connector portion 407. The fourth connector portion 407 is generally configured to be inserted into or otherwise retained within the second connector portion 403, and to provide the inlet passageway 411 for the supply of gas (e.g., ozone) into a reservoir. In addition, the fourth connector portion is configured to provide a portion of the outlet passageway 413 for the removal of gas (e.g., ozone) from the reservoir.

Figure 4K:
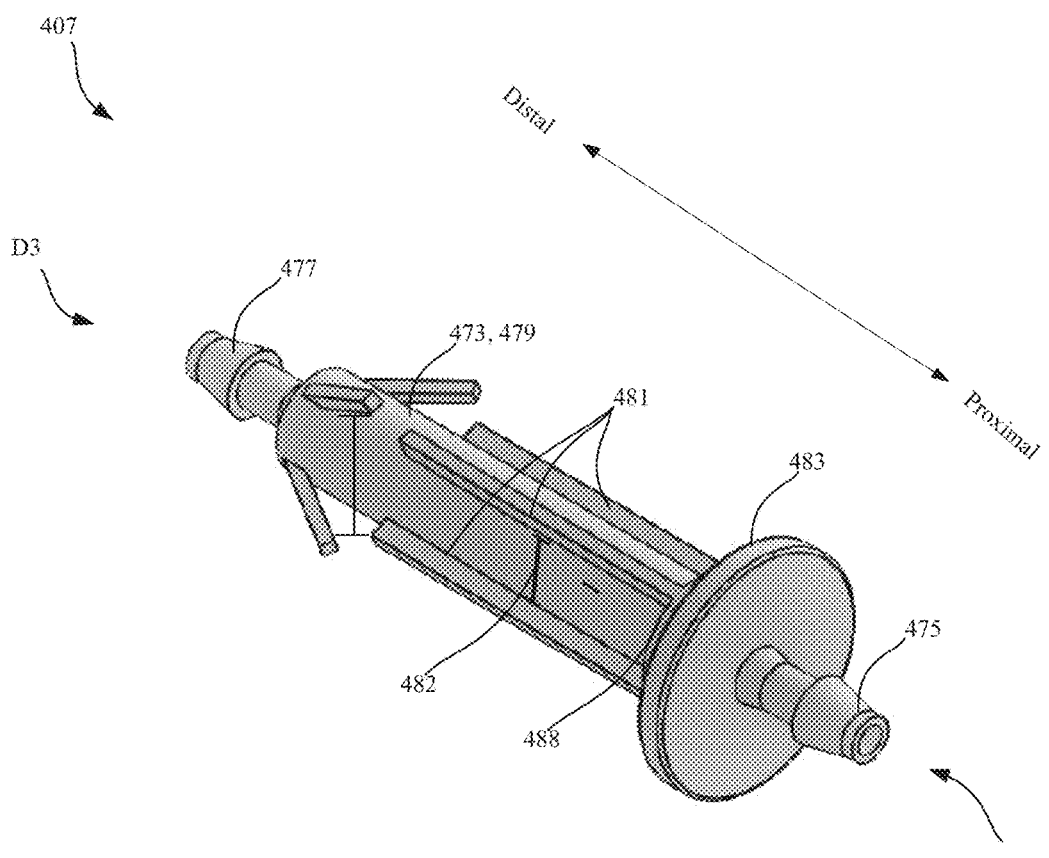
FIG. 4K is a perspective view of a fourth connector portion consistent with the present disclosure.

FIG. 4K depicts one example of a fourth connector portion 407 consistent with the present disclosure. As shown, the fourth connector portion 407 includes a third body 473 having a proximal end P3 and a distal end D3. A first inlet connector 475 is disposed at the proximal end P3, a second inlet connector 477 is disposed at the distal end D3, and a flange 483 is disposed near the proximal end P3. As best shown in FIG. 4C, the inlet passageway 411 is formed through the fourth connector portion and extends between first and second inlet connectors 475, 477. Thus, a proximal end 489 of the inlet passageway 411 is present within the first inlet connector 475, and a distal end 491 of the inlet passageway is present within the second inlet connector. A gas supply (e.g., ozone device 101) may therefore be coupled to first inlet connector 475, and may be used to provide gas (e.g., ozone) to the first inlet connector 475 for conveyance through the inlet passageway 411 and to the second inlet connector 477.

As best shown in FIGS. 4C and 4E, the third body 473 has an outer diameter OD3 (not labeled) that is smaller than the inner diameter ID2 of the proximal portion of the second connector portion 403. As a result, a distal portion of the third body 473 (e.g., distal of the flange 483) may be inserted into the first passageway 429 of the second connector portion 403. The distal portion of the third body 473 may be configured such that when it is fully inserted into the first passageway 429, the second inlet connector 477 extends past the circumferential edge 437 of the second connector portion 403. In that position, an engagement surface 485 of the fourth connector portion 407 (e.g., a portion of the flange 483) may abut a corresponding abutment surface 443 of the second connector portion 403. In some embodiments, at least a portion of the flange 483 may also abut and/or contact a portion of the third connector portion 405, e.g., a proximal circumferential edge 468 thereof.

As best shown in FIG. 4C when the fourth connector portion 407 is fully inserted into the first passageway 429, a gap is present between the inner surface 431 of the wall 433 of the second connector portion 403 and the outer surface 479 of the third body 473 of the fourth connector portion 407. That gap forms a portion of an outlet passageway 413 for the removal of gas from a reservoir.

In the embodiment of FIGS. 4A-4K the distal end 493 of the outlet passageway 413 is or includes opening that is present between the outer surface 479 of the third body 473 and the circumferential edge 437 of the second connector portion 403, and the proximal end 495 of the outlet passageway 413 is present in the outlet port 457. From the distal end 493 the outlet passageway 413 extends, via the gap between the inner surface 431 and the outer surface 479, proximally towards the flange 483. At least a portion of the outlet passageway 413 is therefore disposed radially around the inlet passageway 411. Near the flange 483 the outlet passageway extends through one or more proximal openings 445 in the second connector portion 403 and into the circumferential gap between the inward facing surface 467 of the third body 463 and the outward facing surface 434 of the second body 427. The outlet passageway 413 then continues via the gap to outlet opening 459, which is coupled to outlet port 457.

Accordingly, a gas inflow 497 may be supplied from the first inlet connector 475 to the second inlet connector 477 via the inlet passageway 411 and into a reservoir. Similarly, a gas outflow 499 may be drawn from a reservoir into the distal end 493 of the outlet passageway 413, to the proximal end 495 of the outlet passageway, and ultimately out of the connector unit 400.

To maintain the gap between the inner surface 431 and the outer surface 479, in some embodiments the fourth connector portion may include one or more standoff elements. That concept is shown in FIGS. 4D, 4E, and 4K, which depict fourth connector portion 407 as including a plurality of standoff elements 481. As shown, the each of the standoff elements 481 extends from an outer surface 479 of the third body 473.

The standoff elements 481 are each configured to partially or fully bridge the gap between the inner surface 431 and outer surface 479 when the fourth connector portion 407 is inserted into the first passageway 429 of the second connector portion 403. In such instances a channel 482 may be present between a respective two of the plurality of standoff elements 481. As shown in FIG. 4E, the fourth connector portion 407 may be aligned such that when it is inserted into the first passageway 429, at least one proximal opening 445 in the second connector portion 403 is disposed between two of the standoff elements 481, i.e., such that it is in fluid communication with a channel 488. A gas in gas outflow 499 may then travel from a channel 488 into a proximal opening 445, into the circumferential gap (described above), and then into the outlet opening 459.

As noted above the fourth connector portion 407 includes a flange 483 that abuts at least a portion of the second connector portion 403 when the fourth connector portion 407 is fully inserted therein. In some embodiments, the flange 483 may include a plug 488. The plug 488 may be have an outside diameter OD4 (not shown) that is less than the inside diameter ID2 of the proximal end P2 of the second connector portion 403. Thus when the fourth connector portion 407 is fully inserted into the second connector portion 403, an outward facing surface of the plug 488 may abut and/or contact the inner surface of wall 433, as shown in FIG. 4C. In addition, one or more sealing elements 490 (e.g., O-rings, adhesive, polymers, or other sealing elements) may be disposed between the plug 488, flange 483, and the inward facing surface 433, e.g., to provide a gas-tight seal between such elements.

In some embodiments the fourth connector portion 407 may also include one or more retention elements. When used, the retention elements may be configured to facilitate retention of the fourth connector portion 407 within the second connector portion 403. More particularly, in some embodiments the retention elements may be configured to hinder or prevent lateral movement of the fourth connector portion 407 once it is fully inserted into the second connector portion 403. Non-limiting examples of suitable retention elements that may be used include detents, protuberances, other engagement elements, combinations thereof, and the like. With that in mind, FIGS. 4A-4E, 4K, 6A, and 6B depict embodiments in which the fourth connector portion 407 includes retention elements in the form of deformable protrusions 487 (e.g., deformable wings).

As will be appreciated from the figures, the deformable protrusions 487 may be configured to bend, collapse, or otherwise deform in a first direction (e.g., proximally towards first inlet connector 475) from an expanded position into a compressed position. In the expanded position the deformable protrusions 487 may be larger than the inside diameter ID2 of the first passageway 429 in the second connector portion 403. As a result, the deformable protrusions 487 may deform into the compressed position when the fourth connector portion is inserted and urged into the proximal end of the first passageway 429.

The deformable protrusions 487 may remain in the collapsed/compressed position until they are advanced past the distal end of the first passageway 429, at which time they may return to the expanded (e.g., decompressed) position. Thereafter, removal of the fourth connector portion 407 from the first passageway 429 may be hindered and/or prevented by the deformable protrusions 429. Moreover, the deformable protrusions may resist deformation in a second direction (e.g., distally in a direction towards second inlet connector 477.

Figure 5:
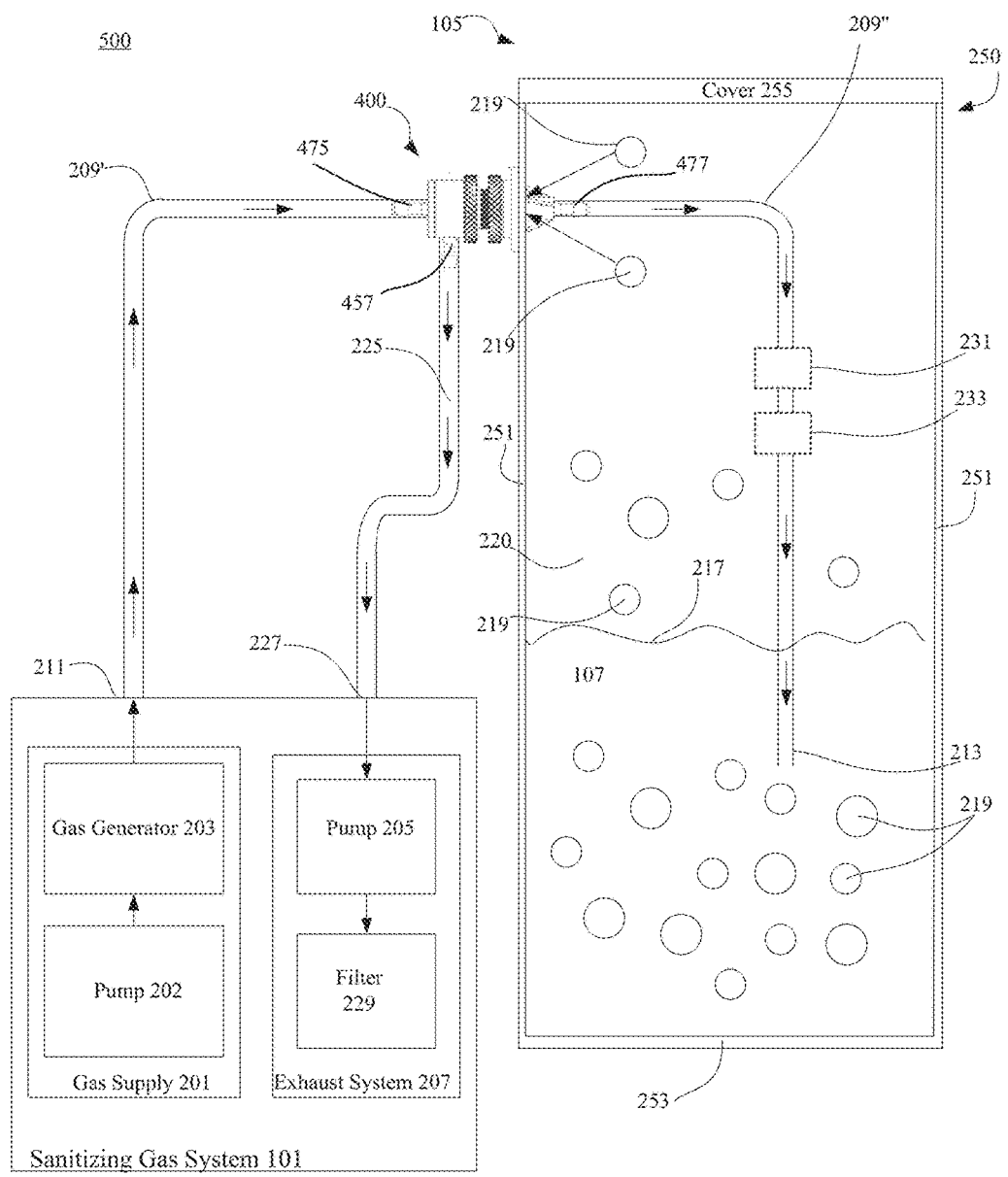
FIG. 5 illustrates an example reservoir sanitization system including the double wall connector unit of FIGS. 4A-4K.

FIG. 5 depicts one example of a reservoir sanitization system utilizing the self-drilling double wall connector unit 400 of FIGS. 4A-4K. The nature and function of many of the elements of FIG. 5 are the same as those shown in FIG. 2 and described above, so a detailed description of such elements is not reiterated in the interest of brevity. As shown, system 500 includes an ozone device 101 and a self-drilling, double wall connector unit 400, which in this embodiment is depicted as installed within a wall 251 of a reservoir 250.

Installation of the connector unit 400 into wall 251 may be accomplished in any suitable manner. For example and consistent with the foregoing description of FIGS. 4A-4K, installation of the connector unit 400 may begin by coupling a first connector portion 401 thereof to the wall 251 (e.g., via an adhesive). A distal end of a second connector portion 403 may be inserted into an opening in the first connector portion 401. The second connector portion 403 may then be rotated to advance the distal end thereof through the opening in the first connector portion, until self-drilling elements on the distal end contact an outer surface of the wall 251. The second connector portion 403 may then continue to be rotated to cause the self-drilling elements to form a hole in the wall 251. In some embodiments at least a portion of the distal end of the second connector portion may be disposed within an interior of the reservoir 250 following the formation of the hole. One or more locking elements may then be employed to lock the position of the second connector portion 203 and the first connector portion 201 relative to one another.

After the hole is formed a third connector portion 405 may be disposed over the proximal end second connector portion 403. A fourth connector portion 407 may then be inserted into a proximal end of a first passageway extending through the second connector portion. The fourth connector portion 407 may include retaining elements that deform from an expanded to a compressed position while a distal end of the fourth connector portion 407 is inserted into the first passageway in the second connector portion 403. When the fourth connector portion 407 is fully inserted, the retaining elements may return to the expanded position, hindering or preventing retraction of the fourth connector portion 407 through the first passageway. A flange on the fourth connector portion 407 may abut and form a gas tight seal with one or more portions of the proximal end of the second connector portion 403 and the third connector portion 405.

As previously described, an inlet passageway 411 is provisioned in the fourth connector portion and extends between a first inlet connector 475 and a second inlet connector 477. In addition, an outlet passageway 413 is provisioned as previously described, and extends between a distal end of the second connector portion and an outlet connector 457.

As shown in FIG. 5, sanitizing gas system 101 includes a gas supply 201 and an exhaust system 207. The gas supply 201 includes a pump 202 and a gas generator 203, and the exhaust system 207 includes a pump 205 and a filter 229. The gas supply 201 is fluidly coupled to the inlet passageway 411 by a first supply line 209', the distal end of which is coupled to the first inlet connector 475. A second supply line 209" is coupled to the second inlet connector 477. The exhaust system 207 is fluidly coupled to the outlet passageway 413 via return line 225, the distal end of which is coupled to the outlet connector 457.

In operation, the gas generator 203 generates sanitizing gas 219 (e.g., ozone). The pump 202 (e.g. an air pump) generates an air flow that causes the sanitizing gas to be conveyed to the first supply line 209', into the inlet passageway 411, and into the second supply line 209". The sanitizing gas 219 exits the distal end 213 of the second supply line 209" to sanitize the interior of the reservoir 250 and any liquid therein, as described above in connection with FIG. 2. The pump 205 (e.g., a vacuum pump) operates to draw excess sanitizing gas 219 from the interior of the reservoir 250 into a distal end 493 of the outlet passageway 413, through the outlet passageway 413, through outlet connector 457, and into return line 225. The excess sanitizing gas 219 may then be conveyed to the filter 229, which may remove the excise sanitizing gas 219 or convert it to another composition. For example where the sanitizing gas 219 is ozone, the filter 229 may be configured to convert at least a portion of the ozone to oxygen.

Figure 7:
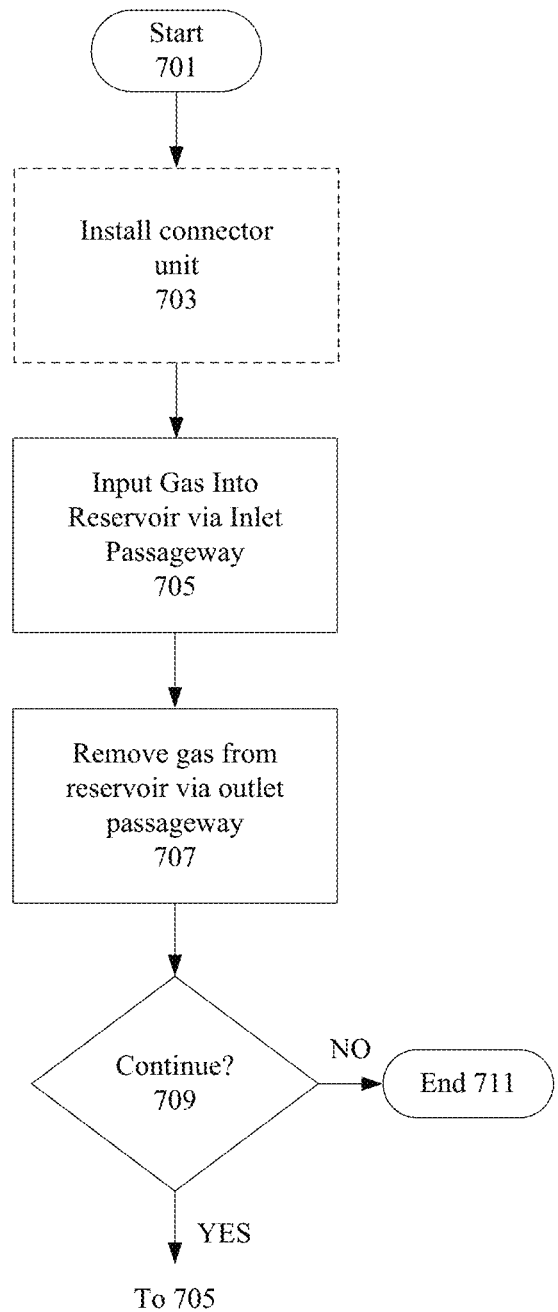
FIG. 7 is a flow chart of example operations of one example of a reservoir sanitization method consistent with the present disclosure.

Another aspect of the present disclosure relates to methods for sanitizing a reservoir, such but not limited to a reservoir of a (e.g., hot) beverage maker. In that regard reference is made to FIG. 7, which is a flow chart of example operations of one example of a reservoir sanitization method consistent with the present disclosure. As shown, the method 700 begins at block 701. The method may then advance to optional block 703, pursuant to which a connector unit consistent with the present disclosure may be installed in a portion of a reservoir (e.g., of a hot beverage maker). For example, operations pursuant to block 703 may include installing a double wall connector unit or a self-drilling, double wall connector unit consistent with the present disclosure into a wall, bottom, top, or lid of a reservoir, as previously described.

Following the operations of block 703 or if block 703 is omitted (e.g. where a connector unit has been previously installed), the method may proceed to block 705. Pursuant to block 705 a sanitizing gas may be provided into a reservoir via an inlet passageway of the connector unit, e.g., as described above. Operations pursuant to block 705 may therefore include generating a sanitizing gas with a gas generator, causing the sanitizing gas to flow into a first supply line, into the inlet passageway, into a second supply line, and into the interior of the reservoir, as previously described. At least a portion of the sanitizing gas so provided may sanitize the interior of the reservoir, including any liquid (e.g., water therein).

The method may then advance to block 707, pursuant to which excess sanitizing gas may be removed from the interior of the reservoir. Operations pursuant to block 707 may therefore include drawing sanitizing gas from the interior of the reservoir into a distal opening of the outlet passageway, through the outlet passageway, through an outlet connector, and to a return line. The operations pursuant to block 707 may also include conveying the sanitizing gas to a filter, as discussed above.

Following the operations of block 707 the method may proceed to block 709, pursuant to which a decision may be made as to whether the method is to continue. The outcome of the decision block 709 may be contingent on a sensor signal provided, e.g., by an optional sensor 233 or on some other criteria. In any case if the method is to continue it may loop back to block 705. But if not, the method may proceed to block 711 and end.

The following examples pertain to additional non-limiting embodiments of the present disclosure.

Example 1

According to this example there is provided a system for sanitizing a hot beverage maker with a water reservoir including: a gas supply system configured to supply a sanitizing gas; a connector unit including an inlet passageway and an outlet passageway, the inlet passageway including a first proximal end and first distal end and the outlet passageway including a second proximal end and a second distal end; and an exhaust system configured to remove the sanitizing gas; wherein: at least a portion of the outlet passageway is disposed radially around the inlet passageway; the gas supply system is configured to fluidly couple to the inlet passageway and the exhaust system is configured to fluidly couple to the outlet passageway; the connector unit is configured to be installed into and span a portion of a reservoir such that the first and second proximal ends are located outside the reservoir and the first and second distal ends are located inside the reservoir when the connector unit is installed; and the gas supply system is configured to supply the sanitizing gas to an inside of the reservoir via the inlet passageway and the exhaust system is configured to remove the sanitizing gas from the inside the reservoir via the outlet passageway.

Example 2

This example includes any or all of the features of example 1, and further includes: a first inlet connector coupled to the first proximal end; a second inlet connector coupled to the first distal end; a first supply line configured to fluidly couple the gas supply system to the inlet passageway via the first inlet connector; and a second supply line configured to couple to the second inlet connector.

Example 3

This example includes any or all of the features of example 2, wherein the second supply line includes a proximal end configured to couple to the second connector and a distal end configured to be disposed beneath any liquid in the reservoir.

Example 4

This example includes any or all of the features of example 2, and further includes: an outlet connector configured to couple to the second proximal end; and a return line configured to couple to the outlet connector so as to fluidly couple the exhaust system to the outlet passageway.

Example 5

This example includes any or all of the features of example 1, wherein the second distal end is located proximal to the first distal end.

Example 6

This example includes any or all of the features of example 2, wherein the second inlet connector includes the first distal end, and the second distal end is located proximal to the first distal end.

Example 7

This example includes any or all of the features of example 1, wherein the connector unit is a self-drilling connector unit.

Example 8

This example includes any or all of the features of example 1, wherein: the connector unit includes a second connector portion including a first passageway and a fourth connector portion configured to be inserted into the first passageway; the fourth connector portion includes a first body and a flange, the first body including an outer surface; and the inlet passageway is formed through the first body.

Example 9

This example includes any or all of the features of example 8, wherein: the second connector portion includes a second body including a wall having an inward facing surface that defines at least a portion of the first passageway; wherein when the fourth connector portion is inserted into the first passageway, a gap is present between the outer surface of the first body and the inward facing surface of the wall of the second body; and the gap defines at least a portion of the outlet passageway

Example 10

This example includes any or all of the features of example 9, further including at least one standoff element extending from the outer surface of the first body, the at least one standoff element to maintain the gap between the outer surface of the first body and inward facing surface of the second body when the fourth connector portion is inserted in the first passageway.

Example 11

This example includes any or all of the features of example 9, wherein: the wall of the second body includes a distal portion and a proximal portion; the second connector portion includes an abutment surface at an edge of proximal portion of the wall of the second body; and an engagement surface of the flange is configured to abut the abutment surface of the second connector portion when the fourth connector portion is inserted into the first passageway

Example 12

This example includes any or all of the features of example 11, wherein: the flange further includes a plug; and the connector unit further includes at least one sealing element; wherein: when the fourth connector portion is inserted into the first passageway: the plug is disposed within a proximal end of the first passageway; and the at least one sealing element is disposed between an inward facing surface of the proximal portion of the wall of the second body and at least a portion of the plug, so as to form a gas-tight seal between at least the plug and the second body.

Example 13

This example includes any or all of the features of example 9, wherein: the first passageway includes a proximal opening and a distal opening; the second connector portion includes self-drilling elements disposed about the distal opening; and the self-drilling elements are configured to form a hole in a portion of the reservoir when the second connector portion is rotated.

Example 14

This example includes any or all of the features of example 9, wherein: the connector unit further includes a first connector portion that is configured to couple to a portion of the reservoir; the first connector portion includes an opening; and the second connector portion is configured to be inserted into the opening of the first connector portion.

Example 15

This example includes any or all of the features of example 14, wherein: the first connector portion includes first guide elements within the opening; the wall of the second body includes a distal portion and a proximal portion; second guide elements are formed on an outside surface of the distal portion of the wall of the second body; and the second guide elements and first guide elements are configured to draw the distal portion of wall of the second body into the opening of the first connector portion.

Example 16

This example includes any or all of the features of example 15, wherein: the first guide elements are first threads; and the second guide elements are second threads configured to threadably engage with the first threads to draw the second body into the opening of the first connector portion when the second connector portion is rotated about an axis that is parallel to and extends through the first passageway.

Example 17

This example includes any or all of the features of example 9, wherein the wall of the second body includes a distal portion and a proximal portion, and at least one proximal hole is present through the proximal portion, the at least one proximal hole forming at least a portion of the outlet passageway.

Example 18

This example includes any or all of the features of example 17, and further includes: a third connector portion including a collar defining an opening, the collar including a proximal edge, at least one spacer element disposed within the opening, and at least one outlet opening; wherein: the collar is configured to be disposed over the proximal portion of the wall of the second body; when the collar is disposed over the proximal portion of the wall of the second body, the at least one spacer element is disposed between an inward facing surface of the collar and the outward facing surface of the proximal portion of the wall, such that a circumferential gap is present between the inward facing surface of the collar and the outward facing surface of the proximal portion of the wall, the circumferential gap fluidly coupling the at least one proximal hole with the at least one outlet opening; the circumferential gap and the outlet opening form at least a portion of the outlet passageway.

Example 19

This example includes any or all of the features of example 18, wherein: the collar of the third connector portion includes a proximal circumferential edge; and when the collar is disposed over the proximal portion of the wall of the second body and the fourth connector portion is inserted into the first passageway, at least a portion of the flange of the fourth connector portion abuts the proximal circumferential edge.

Example 20

This example includes any or all of the features of example 15, and further includes at least one locking element configured to be disposed on the outside surface of the distal portion of the wall of the second body, wherein the at least one locking element is configured to lock the relative position of the first connector portion and the second connector portion.

Example 21

This example includes any or all of the features of example 20, wherein the second connector portion includes a handle, and the at least one locking element is between the handle and the first connector portion.

Example 22

This example includes any or all of the features of example 20, wherein: the at least one locking element includes a first locking element and a second locking element; the first locking element configured to be disposed distally from the first connector portion; and the second locking element is configured to be disposed proximally from the first connector portion.

Example 23

This example includes any or all of the features of example 1, wherein the sanitizing gas is ozone.

Example 24

This example includes any or all of the features of example 1, wherein the gas supply system includes a sanitizing gas generator and an air pump, the air pump configured to generate an air flow for advancing the ozone gas to the inlet passageway and into the reservoir.

Example 25

This example includes any or all of the features of example 24, wherein the sanitizing gas is ozone and the sanitizing gas generator is an ozone generator.

Example 26

This example includes any or all of the features of example 1, wherein the exhaust system includes a vacuum pump and a filter, wherein the vacuum pump is configured to draw the sanitizing gas into the second distal end, through the outlet passageway, and to the filter.

Example 27

This example includes any or all of the features of example 26, wherein the sanitizing gas is ozone, and the filter is configured to convert ozone to oxygen.

Example 28

This example includes any or all of the features of example 27, wherein the filter is a magnesium oxide filter, an activated carbon filter, or a combination thereof.

Example 29

This example includes any or all of the features of example 1, and further includes a sanitizing gas system, the sanitizing gas system including a housing, the gas supply system, and the exhaust system, wherein the gas supply system and the exhaust system are disposed within the housing.

Example 30

According to this example there is provided a system for sanitizing a hot beverage maker, the system including: a gas supply including an ozone generator; an exhaust system; and a self-drilling connector unit configured to traverse a wall of a water reservoir of the hot beverage maker; wherein: the self-drilling connector unit includes a first wall and a second wall; the first wall includes an inlet passageway to provide ozone gas to an interior of the reservoir, the inlet passageway extending from a proximal end to a distal end of the self-drilling connector unit; the self-drilling connector unit further includes an outlet passageway between the first wall and the second wall, the outlet passageway to remove ozone gas from the interior of the reservoir; a proximal end of the inlet passageway is fluidly coupled to the ozone generator; and a proximal end of the outlet passageway is fluidly coupled to the exhaust system.

Example 31

This example includes any or all of the features of example 30, wherein at least a portion of the outlet passageway is disposed radially around the inlet passageway.

Example 32

This example includes any or all of the features of example 30, and further includes self-drilling elements disposed on a distal edge of the outlet passageway.

Example 33

This example includes any or all of the features of example 30, further including first threads on an outside surface of the second wall.

Example 34

This example includes any or all of the features of example 33, wherein: the connector unit further includes a flange configured to couple to the wall of the reservoir; the flange including an opening and second threads within the opening; and the second threads and first threads are threadably coupled with one another such that at least a portion of the second wall is disposed within the opening of the flange.

Example 35

This example includes any or all of the features of example 30, wherein the exhaust system includes a pump for drawing ozone gas from the interior of the reservoir through the outlet passageway and a filter for converting ozone gas removed from the reservoir to oxygen.

Example 36

This example includes any or all of the features of example 35 wherein the filter is an activated carbon filter, a magnesium oxide filter, or a combination thereof.

Example 37

This example includes any or all of the features of example 30, and further includes a sensor for sensing ozone gas in the water reservoir.

Example 38

This example includes any or all of the features of example 30, and further includes a sensor for sensing contaminants in the water reservoir.

Example 39

This example includes any or all of the features of example 30, wherein the proximal end of the inlet passageway is fluidly coupled to the ozone generator by a first inlet line and a distal end of the inlet passageway is coupled to a second inlet line, and the system further includes a check valve to prevent backflow of liquid in the reservoir into the connector unit via the second inlet line.

Example 41

According to this example there is provided a method of sanitizing a water reservoir of a hot beverage maker, including: coupling a connector unit to a wall, lid, or bottom of the reservoir, the connector unit including an inlet passageway and an outlet passageway, the inlet passageway including a first proximal end and first distal end and the outlet passageway including a second proximal end and a second distal end, wherein at least a portion of the outlet passageway is disposed radially around the inlet passageway, the first and second proximal ends are disposed outside the reservoir, and the first and second distal ends are disposed inside the reservoir; fluidly coupling the first proximal end to a gas supply; fluidly coupling the second proximal end to an exhaust system; generating a sanitizing gas with the gas supply; supplying the sanitizing gas to an interior of the reservoir via the inlet passageway; and removing, with the exhaust system, at least a portion of the sanitizing gas from the interior of the reservoir via the outlet passageway.

Example 41

This example includes any or all of the features of example 40, wherein the connector unit further includes a first inlet connector coupled to the first proximal end and an outlet connector coupled to the second proximal end; wherein: fluidly coupling the first proximal end includes fluidly coupling a first supply line to the first inlet connector and to the gas supply; and fluidly coupling the second proximal end includes fluidly coupling a return line to the outlet connector and to the exhaust system.

Example 42

This example includes any or all of the features of example 41, wherein the connector unit further includes a second inlet connector coupled to the first distal end, and the method further includes fluidly coupling a second supply line to the second inlet connector.

Example 43

This example includes any or all of the features of example 42, further including disposing a distal end of the second supply line below a surface of any water in the reservoir.

Example 44

This example includes any or all of the features of example 40, wherein the second distal end is located proximal to the first distal end.

Example 45

This example includes any or all of the features of example 40, wherein the connector unit is a self-drilling connector unit.

Example 46

This example includes any or all of the features of example 40, wherein: the connector unit includes a second connector portion including a first passageway and a fourth connector portion configured to be inserted into the first passageway; the fourth connector portion includes a first body and a flange, the first body including an outer surface; and the inlet passageway is formed through the first body.

Example 47

This example includes any or all of the features of example 46, wherein: the second connector portion includes a second body including a wall having an inward facing surface that defines at least a portion of the first passageway; wherein a gap is present between the outer surface of the first body and the inward facing surface of the wall of the second body; and the gap defines at least a portion of the outlet passageway.

Example 48

This example includes any or all of the features of example 46, wherein the connector unit further includes at least one standoff element extending from the outer surface of the first body, the at least one standoff element configured to maintain the gap between the outer surface of the first body and the inward facing surface of the second body.

Example 49

This example includes any or all of the features of example 46, wherein: the wall of the second body includes a distal portion and a proximal portion; the second connector portion includes an abutment surface at an edge of proximal portion of the wall of the second body; and an engagement surface of the flange abuts the abutment surface of the second connector portion.

Example 50

This example includes any or all of the features of example 49, wherein: the flange further includes a plug; and the connector unit further includes at least one sealing element; the plug is disposed within a proximal end of the first passageway; and the at least one sealing element is disposed between an inward facing surface of the proximal portion of the wall of the second body and at least a portion of the plug and forms a gas-tight seal between at least the plug and the second body.

Example 51

This example includes any or all of the features of example 47, wherein: the first passageway includes a proximal opening and a distal opening; the second connector portion includes self-drilling elements disposed about the distal opening; and the self-drilling elements are configured to form a hole in a portion of the reservoir when the second connector portion is rotated.

Example 52

This example includes any or all of the features of example 47, wherein: the connector unit further includes a first connector portion; the first connector portion includes an opening; and at least part of the second connector portion is disposed within the opening of the first connector portion; wherein coupling the connector unit to the wall includes coupling the first connector portion to the wall.

Example 53

This example includes any or all of the features of example 52, wherein: the first connector portion includes first guide elements within the opening; the wall of the second body includes a distal portion and a proximal portion; second guide elements are formed on an outside surface of the distal portion of the wall of the second body; and coupling the connector unit to the wall of the reservoir includes drawing the distal portion of wall of the second body into the opening of the first connector portion via the first and second guide elements.

Example 54

This example includes any or all of the features of example 53, wherein: the first guide elements are first threads; the second guide elements are second threads; and coupling the connector unit to the wall includes threadably engaging the second threads with the first threads and rotating the second connector portion to draw the second body into the opening of the first connector portion.

Example 55

This example includes any or all of the features of example 47, wherein the wall of the second body includes a distal portion and a proximal portion, and at least one proximal hole is present through the proximal portion, the at least one proximal hole forming at least a portion of the outlet passageway.

Example 56

This example includes any or all of the features of example 55, wherein the connector unit further includes: a third connector portion including a collar defining an opening, the collar including a proximal edge, at least one spacer element disposed within the opening, and at least one outlet opening; wherein: the collar is disposed over the proximal portion of the wall of the second body with the at least one spacer element disposed between an inward facing surface of the collar and the outward facing surface of the proximal portion of the wall; a circumferential gap is present between the inward facing surface of the collar and the outward facing surface of the proximal portion of the wall, the circumferential gap fluidly coupling the at least one proximal hole with the at least one outlet opening; and the circumferential gap and the outlet opening form at least a portion of the outlet passageway.

Example 57

This example includes any or all of the features of example 56, wherein: the collar of the third connector portion includes a proximal circumferential edge; and at least a portion of the flange of the fourth connector portion abuts the proximal circumferential edge.

Example 58

This example includes any or all of the features of example 48, wherein: the connector unit further includes at least one locking element disposed on the outside surface of the distal portion of the wall of the second body; and coupling the connector unit to the wall of the reservoir includes locking the relative position of the first connector portion and the second connector portion with the at least one locking element.

Example 59

This example includes any or all of the features of example 58, wherein the second connector portion includes a handle and the at least one locking element is between the handle and the first connector portion.

Example 60

This example includes any or all of the features of example 58, wherein: the at least one locking element includes a first locking element and a second locking element; the first locking element configured to be disposed distally from the first connector portion; and the second locking element is configured to be disposed proximally from the first connector portion.

Example 61

This example includes any or all of the features of example 40, wherein the sanitizing gas is ozone.

Example 62

This example includes any or all of the features of example 61, wherein: the gas supply system includes an ozone gas generator and an air pump; generating the sanitizing gas includes generating ozone gas with the ozone gas generator; supplying the sanitizing gas to the interior of the reservoir includes generating an air flow with the air pump to cause the ozone gas to advance through the inlet passageway into the interior of the reservoir.

Example 63

This example includes any or all of the features of example 40, wherein: the exhaust system includes a vacuum pump and a filter; removing at least a portion of the sanitizing gas includes drawing, with the vacuum pump, at least a portion of the sanitizing gas from the interior of the reservoir through the outlet passageway and to the filter.

Example 64

This example includes any or all of the features of example 63, wherein the sanitizing gas is ozone, and the method further includes converting the ozone to oxygen with the filter.

Example 65

This example includes any or all of the features of example 64, wherein filter is a magnesium oxide filter, an activated carbon filter, or a combination thereof.

Example 66

This example includes any or all of the features of example 64, wherein filter is a magnesium oxide filter, an activated carbon filter, or a combination thereof.

The technologies described herein may also be configured to provide an easy to install entry port into a reservoir of a beverage maker. For example, a connector unit consistent with the present disclosure may be embedded in an ozone device. The ozone device may be configured to automatically insert the connector unit into a portion (e.g., sidewall) of the reservoir in response to a user input. Connector units consistent with the present disclosure may also be manually or automatically inserted into a wall or other portion of a reservoir, with a saddle shaped valve or other similar valve that includes openings or otherwise configured to provide additional ports and/or connectors that enable the placement of one or more distribution lines into the reservoir. While the above described FIGS. depict certain configurations of connector units that may be used, any suitable connector unit having an entry channel for a sanitizing gas and an exit channel for the sanitizing gas may be used.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications.

What is claimed is:

1. A system for sanitizing a hot beverage maker with a water reservoir comprising:
   a gas supply system configured to supply a sanitizing gas;
   a connector unit comprising an inlet passageway and an outlet passageway, the inlet passageway comprising a first proximal end and first distal end and the outlet passageway comprising a second proximal end and a second distal end; and
   an exhaust system configured to remove the sanitizing gas;
wherein:
   at least a portion of the outlet passageway is disposed radially around the inlet passageway;
   the gas supply system is configured to fluidly couple to the inlet passageway and the exhaust system is configured to fluidly couple to the outlet passageway;
   the connector unit is configured to be installed into and span a portion of a reservoir such that the first and second proximal ends are located outside the reservoir and the first and second distal ends are located inside the reservoir when the connector unit is installed;
   the gas supply system is configured to supply the sanitizing gas to an inside of the reservoir via the inlet passageway and the exhaust system is configured to remove the sanitizing gas from the inside the reservoir via the outlet passageway;
   the connector unit comprises a second connector portion comprising a first passageway and a fourth connector portion configured to be inserted into the first passageway;
   the fourth connector portion comprises a first body and a flange, the first body comprising an outer surface; and
   the inlet passageway is formed through the first body.

2. The system of claim 1, further comprising:
   a first inlet connector coupled to the first proximal end;
   a second inlet connector coupled to the first distal end;
   a first supply line configured to fluidly couple the gas supply system to the inlet passageway via the first inlet connector; and
   a second supply line configured to couple to the second inlet connector.

3. The system of claim 2, wherein the second supply line comprises a proximal end configured to couple to the second connector and a distal end configured to be disposed beneath any liquid in the reservoir.

4. The system of claim 2, further comprising:
   an outlet connector configured to couple to the second proximal end; and
   a return line configured to couple to the outlet connector so as to fluidly couple the exhaust system to the outlet passageway.

5. The system of claim 1, wherein the second distal end is located proximal to the first distal end.

6. The system of claim 2, wherein the second inlet connector comprises the first distal end, and the second distal end is located proximal to the first distal end.

7. The system of claim 1, wherein the connector unit is a self-drilling connector unit.

8. The system of claim 1, wherein:
   the second connector portion comprises a second body comprising a wall having an inward facing surface that defines at least a portion of the first passageway;
   wherein when the fourth connector portion is inserted into the first passageway, a gap is present between the outer surface of the first body and the inward facing surface of the wall of the second body and the gap defines at least a portion of the outlet passageway.

9. The system of claim 8, further comprising at least one standoff element extending from the outer surface of the first body, the at least one standoff element to maintain the gap between the outer surface of the first body and inward facing surface of the second body when the fourth connector portion is inserted in the first passageway.

10. The system of claim 8, wherein:
the wall of the second body comprises a distal portion and a proximal portion;
the second connector portion comprises an abutment surface at an edge of proximal portion of the wall of the second body; and
an engagement surface of the flange is configured to abut the abutment surface of the second connector portion when the fourth connector portion is inserted into the first passageway.

11. The system of claim 10, wherein:
the flange further comprises a plug; and
the connector unit further comprises at least one sealing element;
wherein:
when the fourth connector portion is inserted into the first passageway:
the plug is disposed within a proximal end of the first passageway; and
the at least one sealing element is disposed between an inward facing surface of the proximal portion of the wall of the second body and at least a portion of the plug, so as to form a gas-tight seal between at least the plug and the second body.

12. The system of claim 8, wherein:
the first passageway comprises a proximal opening and a distal opening;
the second connector portion comprises self-drilling elements disposed about the distal opening; and
the self-drilling elements are configured to form a hole in a portion of the reservoir when the second connector portion is rotated.

13. The system of claim 8, wherein:
the connector unit further comprises a first connector portion that is configured to couple to a portion of the reservoir;
the first connector portion comprises an opening; and
the second connector portion is configured to be inserted into the opening of the first connector portion.

14. The system of claim 13, wherein:
the first connector portion comprises first guide elements within the opening;
the wall of the second body comprises a distal portion and a proximal portion; second guide elements are formed on an outside surface of the distal portion of the wall of the second body; and
the second guide elements and first guide elements are configured to draw the distal portion of wall of the second body into the opening of the first connector portion.

15. The system of claim 14, wherein:
the first guide elements are first threads; and
the second guide elements are second threads configured to threadably engage with the first threads to draw the second body into the opening of the first connector portion when the second connector portion is rotated about an axis that is parallel to and extends through the first passageway.

16. The system of claim 14, further comprising at least one locking element configured to be disposed on the outside surface of the distal portion of the wall of the second body, wherein the at least one locking element is configured to lock the relative position of the first connector portion and the second connector portion.

17. The system of claim 16, wherein the second connector portion comprises a handle, and the at least one locking element is between the handle and the first connector portion.

18. The system of claim 16, wherein:
the at least one locking element comprises a first locking element and a second locking element;
the first locking element configured to be disposed distally from the first connector portion; and
the second locking element is configured to be disposed proximally from the first connector portion.

19. The system of claim 8, wherein the wall of the second body comprises a distal portion and a proximal portion, and at least one proximal hole is present through the proximal portion, the at least one proximal hole forming at least a portion of the outlet passageway.

20. The system of claim 19, further comprising:
a third connector portion comprising a collar defining an opening, the collar comprising a proximal edge, at least one spacer element disposed within the opening, and at least one outlet opening;
wherein:
the collar is configured to be disposed over the proximal portion of the wall of the second body;
when the collar is disposed over the proximal portion of the wall of the second body, the at least one spacer element is disposed between an inward facing surface of the collar and the outward facing surface of the proximal portion of the wall, such that a circumferential gap is present between the inward facing surface of the collar and the outward facing surface of the proximal portion of the wall, the circumferential gap fluidly coupling the at least one proximal hole with the at least one outlet opening;
the circumferential gap and the outlet opening form at least a portion of the outlet passageway.

21. The system of claim 20, wherein:
the collar of the third connector portion comprises a proximal circumferential edge; and
when the collar is disposed over the proximal portion of the wall of the second body and the fourth connector portion is inserted into the first passageway, at least a portion of the flange of the fourth connector portion abuts the proximal circumferential edge.

22. The system of claim 1, further comprising a sanitizing gas system, the sanitizing gas system comprising a housing, the gas supply system, and the exhaust system, wherein the gas supply system and the exhaust system are disposed within the housing.

23. A system for sanitizing a hot beverage maker with a water reservoir comprising:
a gas supply system configured to supply a sanitizing gas;
a connector unit comprising an inlet passageway and an outlet passageway, the inlet passageway comprising a first proximal end and first distal end and the outlet passageway comprising a second proximal end and a second distal end; and
an exhaust system configured to remove the sanitizing gas;

wherein:
at least a portion of the outlet passageway is disposed radially around the inlet passageway;
the gas supply system is configured to fluidly couple to the inlet passageway and the exhaust system is configured to fluidly couple to the outlet passageway;
the connector unit is configured to be installed into and span a portion of a reservoir such that the first and second proximal ends are located outside the reservoir and the first and second distal ends are located inside the reservoir when the connector unit is installed; and
the gas supply system is configured to supply the sanitizing gas to an inside of the reservoir via the inlet passageway and the exhaust system is configured to remove the sanitizing gas from the inside the reservoir via the outlet passageway, wherein the sanitizing gas is ozone.

24. The system of claim 23, wherein the gas supply system comprises a sanitizing gas generator and an air pump, the air pump configured to generate an air flow for advancing the ozone to the inlet passageway and into the reservoir.

25. The system of claim 24, wherein the sanitizing gas is ozone and the sanitizing gas generator is an ozone generator.

26. A system for sanitizing a hot beverage maker with a water reservoir comprising:
a gas supply system configured to supply a sanitizing gas;
a connector unit comprising an inlet passageway and an outlet passageway, the inlet passageway comprising a first proximal end and first distal end and the outlet passageway comprising a second proximal end and a second distal end; and
an exhaust system configured to remove the sanitizing gas;
wherein:
at least a portion of the outlet passageway is disposed radially around the inlet passageway;
the gas supply system is configured to fluidly couple to the inlet passageway and the exhaust system is configured to fluidly couple to the outlet passageway;
the connector unit is configured to be installed into and span a portion of a reservoir such that the first and second proximal ends are located outside the reservoir and the first and second distal ends are located inside the reservoir when the connector unit is installed;
the gas supply system is configured to supply the sanitizing gas to an inside of the reservoir via the inlet passageway and the exhaust system is configured to remove the sanitizing gas from the inside the reservoir via the outlet passageway,
wherein the exhaust system comprises a vacuum pump and a filter, and the vacuum pump is configured to draw the sanitizing gas into the second distal end, through the outlet passageway, and to the filter.

27. The system of claim 26, wherein the sanitizing gas is ozone, and the filter is configured to convert ozone to oxygen.

28. The system of claim 27, wherein the filter is a magnesium oxide filter, an activated carbon filter, or a combination thereof.

* * * * *